United States Patent
Shu et al.

(10) Patent No.: US 6,455,292 B1
(45) Date of Patent: Sep. 24, 2002

(54) FULL-LENGTH SERINE PROTEIN KINASE IN BRAIN AND PANCREAS

(75) Inventors: Youmin Shu, Potomac; Wufang Fan, Germantown; Karl F. Kovacs, Rockville; Michael Zidanic, Derwood; Gilbert Jay, North Bethesda, all of MD (US)

(73) Assignee: OriGene Technologies, Inc, Rockville, MD (US)

( * ) Notice: Subject to any disclaimer, the term of this patent is extended or adjusted under 35 U.S.C. 154(b) by 0 days.

(21) Appl. No.: 09/930,181

(22) Filed: Aug. 16, 2001

(51) Int. Cl.[7] .............................. C12N 9/12; C12N 1/20; C12N 15/63; C12N 5/16; C12Q 1/48
(52) U.S. Cl. ...................... 435/194; 435/15; 435/252.3; 435/320.1; 435/325; 536/23.2
(58) Field of Search .............................. 435/194, 320.1, 435/252.3, 15, 325; 536/23.2

(56) References Cited

PUBLICATIONS

Stanchi et al., GenEMBL accession No. HSA6701, Mar. 14, 2001.*
Lewin, Genes IV, Oxford University Press, 1990.*
Broun et al., Science 282:1315–1317, 1998.*
Brenner, TIG 15:132–1333, 1999.*
Smith et al., Nature Biotechnology 15:1222–1223, 1997.*
Van de Loo et al., Proc. Natl. Acad. Sci. 92:6743–6747, 1995.*
Adams et al., SPTREMBL accession No. Q9VUV4, May 1, 2000, Science 287:2185–2195, 2000.*

* cited by examiner

*Primary Examiner*—Ponnathapuachuta Murthy
*Assistant Examiner*—Delia Ramirez
(74) *Attorney, Agent, or Firm*—Richard M. Lebovitz

(57) ABSTRACT

The present invention relates to all facets of novel polynucleotides, the polypeptides they encode, antibodies and specific binding partners thereto, and their applications to research, diagnosis, drug discovery, therapy, clinical medicine, forensic science, pathology, and medicine. The polynucleotides are expressed in brain and pancreas and are therefore useful in variety of ways, including, but not limited to, as molecular markers, as drug targets, and for detecting, diagnosing, staging, monitoring, prognosticating, preventing or treating, determining predisposition to diseases and conditions, especially relating to brain and pancreas.

6 Claims, 3 Drawing Sheets

```
AJ006701   ------------------------------------------------------------
Kse336-1   MTSTGKDGGAQHAQYVGPYRLEKTLGKGQTGLVKLGVHCVTCQKVAIKIVNREKLSESVL   60

AJ006701   ------------------------------------------------------------   49
Kse336-1   LIEHPHVLKLHDVYENKKYLYLVLEHVSGGELFDYLVKKGRLTPKEARK              120
Kse336-2   MKVEREIAILKLIEHPHVLKLHDVYENKKYLYLVLEHVSGGELFDYLVKKGRLTPKEARK
           MKTKNICRYLVLEHVSGGELFDYLVKKGRLTPKEARK

AJ006701   FFRQIISALDFCHSHSICHRDLKPENLLLDEKNNIRIADFGMASLQVGDSLLETSCGSPH   109
Kse336-1   FFRQIISALDFCHSHSICHRDLKPENLLLDEKNNIRIADFGMASLQVGDSLLETSCGSPH   180
Kse336-2   FFRQIISALDFCHSHSICHRDLKPENLLLDEKNNIRIADFGMASLQVGDSLLETSCGSPH

AJ006701   YACPEVIRGEKYDGRKADVWSCGVILFALLVGALPFDDDNLRQLLEKVKRGVFHMPHFIP   169
Kse336-1   YACPEVIRGEKYDGRKADVWSCGVILFALLVGALPFDDDNLRQLLEKVKRGVFHMPHFIP   240
Kse336-2   YACPEVIRGEKYDGRKADVWSCGVILFALLVGALPFDDDNLRQLLEKVKRGVFHMPHFIP

AJ006701   PDCQSLLRGMSEVDAARRLTLEHIQKHIWYIGGKNEPEPEQPIPRKVQIRSLPSLEDIDP   229
Kse336-1   PDCQSLLRGMIEVDAARRLTLEHIQKHIWYIGGKNEPEPEQPIPRKVQIRSLPSLEDIDP   300
Kse336-2   PDCQSLLRGMIEVDAARRLTLEHIQKHIWYIGGKNEPEPEQPIPRKVQIRSLPSLEDIDP

AJ006701   DVLDSMHSLGCFRDRNKLLQDLLSEEENQEKMIYFLLLDRKERYPSQEDEDLPPRNEIDP   289
Kse336-1   DVLDSMHSLGCFRDRNKLLQDLLSEEENQEKMIYFLLLDRKERYPSQEDEDLPPRNEIDP   360
Kse336-2   DVLDSMHSLGCFRDRNKLLQDLLSEEENQEKMIYFLLLDRKERYPSQEDEDLPPRNEIDP

AJ006701   PRKRVDSPMLNRHGKRRPERKSMEVLSVTDGGSPVPARRAIEMAQHGQRSRSISGASSGL   349
Kse336-1   PRKRVDSPMLNRHGKRRPERKSMEVLSVTDGGSPVPARRAIEMAQHGQRSRSISGASSGL   420
Kse336-2   PRKRVDSPMLNRHGKRRPERKSMEVLSVTDGGSPVPARRAIEMAQHGQRSRSISGASSGL
```

FIG. 2A

```
AJ006701   STSPLSSPRVTPHPSPRGSPLPTPKGTPVHTPKESPAGTPNPTPPSSPSVGGVPWRARLN 409
Kse336-1   STSPLSSPRVTPHPSPRGSPLPTPKGTPVHTPKESPAGTPNPTPPSSPSVGGVPWRARLN 480
Kse336-2   STSPLSSPRVTPHPSPRGSPLPTPKGTPVHTPKESPAGTPNPTPPSSPSVGGVPWRARLN
AF020089

AJ006701   SIKNSFLGSPREFHRRKLQVPTPEEMSNLTPESSPELAKKSWFGNFISLEKEEQIFVVIKD 469
Kse336-1   SIKNSFLGSPREFHRRKLQVPTPEEMSNLTPESSPELAKKSWFGNFISLEKEEQIFVVIKD 540
Kse336-2   SIKNSFLGSPREFHRRKLQVPTPEEMSNLTPESSPELAKKSWFGNFISLEKEEQIFVVIKD
AF020089   ------------------MSNLTPESSPELAKKSWFGNFISLEKEEQIFVVIKD 36

AJ006701   KPLSSIKADIVHAFLSIPSLSHSVISQTSFRAEYKATGGPAVFQKPVKFQVDITYTEGGE 529
Kse336-1   KPLSSIKADIVHAFLSIPSLSHSVISQTSFRAEYKATGGPAVFQKPVKFQVDITYTEGGE 600
Kse336-2   KPLSSIKADIVHAFLSIPSLSHSVISQTSFRAEYKATGGPAVFQKPVKFQVDITYTEGGE
AF020089   KPLSSIKADIVHAFLSIPSLSHSVISQTSFRAEYKATGGPAVFQKPVKFQVDITYTEGGE 96

AJ006701   AQKENGIYSVTFTLLSGPSRRFKRVVETIQAQLLSTHDPPAAQHLSEPPPPAPGLSWGAG 589
Kse336-1   AQKENGIYSVTFTLLSGPSRRFKRVVETIQAQLLSTHDPPAAQHLSDTTN-CMEMMTGRL 659
Kse336-2   AQKENGIYSVTFTLLSGPSRRFKRVVETIQAQLLSTHDPPAAQHLSDTTN-CMEMMTGRL
AF020089   AQKENGIYSVTFTLLSGPSRRFKRVVETIQAQLLSTHDP-----LRPST--CQTPLT--V 147

AJ006701   LKGQKVATSYESSL 603
Kse336-1   SKCGIIPKS----- 668
Kse336-2   SKCGIIPKS
AF020089   WK------ 149
```

FIG. 2B

FULL-LENGTH SERINE PROTEIN KINASE IN BRAIN AND PANCREAS

DESCRIPTION OF THE DRAWINGS

SEQ ID NOS. 1 and 2 show the nucleotide and amino acid sequences of KSE336-1. SEQ ID NOS. 3 and 4 show the nucleotide and amino acid sequences of KSE336-2. The N-terminal amino acid sequence of KSE336-1 is shown in SEQ ID NOS 5 and 6. Promoter sequences for KSE336 are listed in SEQ ID NOS 7–14. SEQ ID NOS. 15 and 16 show substrate for serine kinase activity. The amino acid sequence of AJ006701 is shown in SEQ ID NO 17 and the amino acid sequence of AF020089 is shown in SEQ ID NO 18. These are human cDNAs.

FIGS. 2A and 2B show sequence comparisons between KSE336-1 (SEQ ID NO 2), KSE336-2 (SEQ ID NO 4), AJ00601 (SEQ ID NO 17), and AF020089 (SEQ ID NO 18).

DESCRIPTION OF THE INVENTION

Figure 1:
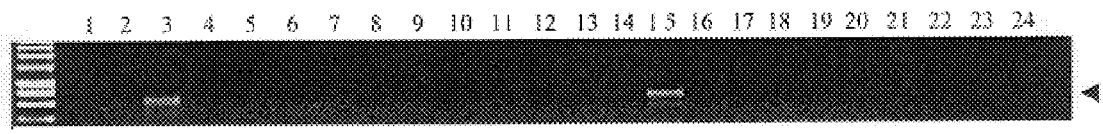
FIG. 1 shows the expression pattern of KSE 336. 1, adrenal gland; 2, bone marrow; 3, brain; 4, colon; 5, heart; 6, intestine; 7, kidney; 8, liver; 9, lung; 10, lymph node; 11 lymphocytes; 12, mammary gland; 13, muscle; 14, ovary; 15, pancreas; 16, pituitary; 17, prostate; 18, skin; 19, spleen; 20, stomach; 21, testis; 22, thymus; 23, thyroid; 24, uterus.

The present invention relates to all facets of novel polynucleotides, the polypeptides they encode, antibodies and specific binding partners thereto, and their applications to research, diagnosis, drug discovery, therapy, clinical medicine, forensic science and medicine, etc. The polynucleotides are expressed in brain and pancreas and are therefore useful in variety of ways, including, but not limited to, as molecular markers, as drug targets, and for detecting, diagnosing, staging, monitoring, prognosticating, preventing or treating, determining predisposition to, etc., diseases and conditions, especially relating to brain and pancreas. The identification of specific genes, and groups of genes, expressed in pathways physiologically relevant to brain and pancreas permits the definition of functional and disease pathways, and the delineation of targets in these pathways which are useful in diagnostic, therapeutic, and clinical applications. The present invention also relates to methods of using the polynucleotides and related products (proteins, antibodies, etc.) in business and computer-related methods, e.g., advertising, displaying, offering, selling, etc., such products for sale, commercial use, licensing, etc.

Kinases

KSE 336 is a protein kinase, exhibiting, e.g., a serine/threonine activity. Protein kinases are a diverse and large group of enzymes that catalyze the transfer of a phosphate group. In most cases, the gamma phosphate of ATP or GTP serves as the phosphate donor, and a protein alcohol or phenol group acts as the phosphate acceptor. Protein kinases are ubiquitous in eukaryotes, playing an important role in development, differentiation, cell division, cell function, and signaling pathways. Kinases can be divided into different groups based on sequence homology and function. These groups include: (1) CMGC, (2) PTK, (3) Pages 8–9, New Science Press.

(1) The CMGC kinases includes cyclin-dependent kinases (Cdks), MAPKs, glycogen synthase kinases (GSKs), and CTD kinases. These enzymes phosphorylate serines and threonines at -Ser-Pro- or -Thr-Pro-.

(2) PTK kinases are the tyrosine kinases. These include receptor kinases having a ligand binding extracellular domain and an intracellular kinase domain, as well as intracellularly expressed PTKs.

(3) The STE group includes homologs of yeast Ste20 (PAK), Ste11 (MAPKKK), and Ste7 (MAPKK). These are serine/threonine kinases, some of which have dual specificity. A major group of the STE kinases are the kinases involved in the mitogen-activated protein kinase (MAPK) cascade. MAPK cascades play key roles in relaying various physiological, environmental, or pathological signals from the environment to the transcriptional machinery in the nucleus. MAPK is activated by dual phosphorylation of threonine and tyrosine residues in a TXY motif located between subdomains VII and VIII of the kinase catalytic domain by MAPK kinase (MAPKK). MAPKK is, in turn, activated by MAPKK kinase (MAPKKK). The general path of the cascade can therefore be characterized as: Stimulus→MAPKKK→MAPKK→MAPK→Response. In *S. cerevisiae*, Ste20, Ste11, and Ste7 form a MAPK cascade which functions in the pheromone-induced signal transmission.

(4) The Gcyc group most closely resembles the kinase-like domain found in guanylate cyclases. The specificity of these enzymes has not been completely characterized.

(5) The AGC group is made up the PKAs (cAMP-dependent protein kinase), PTGs (cGMP-dependent kinase), and certain lipid activated protein kinases (protein kinase C or PKC). They phosphorylate serine or threonine residues. These enzymes are comprised of multiple subunits. For example, PKA consists a catalytic (C) and a regulatory (R) subunit. A PKA can have multiple regulatory and/or catalytic subunits. For instance, mammalian 5' AMP-activated protein kinase (AMPK) comprises a single catalytic alpha-subunit and two noncatalytic subunits, beta- and gamma-. There are multiple isoforms for each subunit. See, e.g., Stapleton et al., *J. Biol. Chem.*, 271:611–614, 1996.

(6) The CAMK group of protein kinases comprise calcium/calmodulin regulated, cAMP-regulated, and ELKL motif kinases. These enzymes phosphorylate serine and threonine residues.

(7) The CK1 group is so named because its family members resemble the casein kinase 1. The function of this class has been difficult to document, but they typically consist of a single catalytic subunit capable of phosphorylating serine residues. Many different isoforms for each type have been described.

KSE336 possesses serine and/or threonine kinase activity similar to the activity displayed by kinases in groups 1, 3, 5, 6, and 7. By its amino acid sequence, it is most similar the AGC (5) group of kinases.

KSE336

KSE336 codes for a serine/threonine kinase ("STK"). Two forms of it have been identified, KSE336-1 (FB1620G06) and KSE336-2 (AB1138D11). KSE336-1 is 668 amino acids, and KSE336-2 is 585 amino acids. Nucleotide and corresponding amino acid sequences of KSE336-1 are shown in SEQ ID NOS. 1 and 2, and SEQ ID NOS 3 and 4 for KSE336-2. The serine threonine kinase domain is found at amino acid positions 19–270 in KSE336-1, and 1–185 in KSE336-2. A protein kinase active-site signature is found at amino acid positions 137–149 in KSE336-1 and is present in KSE336-2, as well. See, FIG. 2. The two forms differ from each other only at the 5' end. See, FIG. 2. The open reading frames differ by only 4 base pairs. Alignment with genomic DNA reveals that this difference is derived from the exon-intron splicing site as follows:

```
Intron 5' donor sequence          Intron 3' accepter sequence

GTAGGT  ------------------------  CAG
        1     2
```

The KSE336-1 cDNA was derived from a transcript that was spliced using the first GT as the 5' donor site, while KSE336-2 was spliced using the second GT as the 5' donor site. As a result, KSE336-2 has 4 more base pairs than KSE336-1. Since this difference occurs in coding sequence, a shift in the open reading frame was observed, as reflected in the different 5' ends. Polymorphisms are shown in Table 2.

KSE336 maps to chromosomal band 11p15.5-pter (physical map from 0.679 to 0.950 Mb; NT_024164.2; AC074189; BAC clone, RP11-371C18). Partial clones, AF020089 and AJ006701, have been identified. See, FIG. 2 for alignment. The present invention relates to fragments comprising overlapping regions, non-overlapping regions, regions comprising variations, etc., between the different forms of KSE336, and any homologs, truncated versions, polymorphisms, etc. Examples of sequences related to KSE36 are shown in FIG. 2. Additional examples are described below. As an illustration, but not to limit the invention in anyway, the present invention relates to such fragments as, amino acid positions 1–71 (SEQ ID NOS 5 and 6) of KSE336-1; amino acid positions 72–668 of KSE336-1; amino acid positions 1–8 of KSE336-2; amino acid positions 647–659 of KSE336-1; 640-644 of KSE-1, 660–668 of KSE336-1, etc. Such fragments can comprise, consist of, or consist essentially of, these sequences.

The polypeptide coded for by KSE336 exhibits sequence identity to other STKs. It is related to kinases from other species are AF240782 (mouse) and AF316542 (Drosophila). It also shares sequence homology with the catalytic subunits of mammalian 5'AMP-activated protein kinase (AMPK) and yeast SNF1. The SNF1 family of PKAs are involved in glucose metabolism. See, e.g., da Silva Xavier et al., *Proc. Natl. Acad. Sci.*, 97:4023–4028, 2000. Mammalian AMPKs appear to be involved in regulating the response to nutritional stress, e.g., when ATP levels are low. See, e.g., Stapleton et al., *J. Biol. Chem.*, 271:611–614, 1996.

KSE336 is also homologous to HrPOPK-1, an STK whose mRNA is detected in early ascidian embryos. Sasakura et al., *Mech. Dev.*, 76:161–163, 1998. Sequence homology is also observed between KSE336 and another STK, SAD-1, a polypeptide which regulates presynaptic vesicle clustering and axon termination in *C. elegans*. See, e.g., *Neuron*, 29(1):115–129,2001.

KSE336 is predicted to have 19 exons with the following structure:

|  |  |
|---|---|
| 2 ... 320 | (NT_024164) |
| 321 ... 413 | (AC074189, RP11-371C18) reverse orientation |
| 414 ... 504 | (NT_024164) |
| 505 ... 641 | (NT_024164) |
| 642 ... 758 | (AC074189) |
| 759 ... 792 | (AC074189) |
| 793 ... 861 | (AC091196, RP11-371C18) |
| 862 ... 1008 | (AC091196) |
| 1009 ... 1041 | (NT_024164) |
| 1042 ... 1206 | (NT_024124) |
| 1207 ... 1304 | (NT_024124) |
| 1305 ... 1455 | (NT_024124) |
| 1456 ... 1516 | (NT_024124) |
| 1517 ... 1724 | (NT_024124) |
| 1725 ... 1773 | (NT_024124) |
| 1774 ... 1897 | (NT_024124) |
| 1898 ... 2078 | (NT_024124) |
| 2079 ... 2168 | (NT_024124) |
| 2169 ... 2263 | (NT_024124) |

Expression

As show in FIG. 1, expression of KSE336 is restricted to the brain and pancreas. The coincidence of brain and pancreas expression is especially interesting since these cell types utilize common signaling pathways during development. Components of the Notch signaling pathway are expressed during both neuronal and pancreatic cell differentiation (Apelqvist et al., *Nature*, 400:877–881, 1999; Jensen et al., *Nature Genet.*, 24:36–44, 2000). Furthermore, embryonic stem (ES) cells which display neuronal cell markers have been induced to differentiate into insulin-producing pancreatic islet cells, indicating a close relationship between the two cell types (Lumelsky et al., *Science*, 292:1389–1394, 2001). Additionally, both tissues are exquisitely sensitive to changes in glucose and ATP levels, a function of cAMP-dependent STKs, such as SNF1 and AMPK. KSE336 is also expressed in neural stem cells.

Disease Association

As indicated by its expression profile, KSE336 has a functional role in brain and pancreas. When the normal function of a gene is perturbed, the cells and tissues in which it is expressed are correspondingly affected, generally in a deleterious way. A range of different phenotypes are commonly observed, depending on the nature of the gene mutation and its interaction with other genetic and environmental factors. The brain and pancreas phenotypes associated with KSE336 aberrations, include, but are not limited to, e.g., astrocytoma, meningioma, pancreatic adenocarcinoma, insulin-dependent diabetes mellitus 2 (IDDM2), helicoid peripapillary chorioretinal degeneration (also known as atrophia areata), Beckwith-Wiedemann syndrome (see, e.g., Hoovers et al., *Proc. Natl. Acad. Sci.*, 92:12456–12460, 1995), and congenital hyperinsulinism (e.g., Fournet et al., *Horm. Res.*, 53:Suppl. 1:2–6, 2000).

In addition to the above-mentioned disorders, KSE336 may be associated with other conditions, e.g., which result from its expression in tissues other than brain or pancreas. Such disorders include, but are not limited to, arthrogryposis multiplex congenital distal type 2B (AMCD2B; Paris et al., *Genomics*, 69(2):196–202, 2000), Wilms Tumor 2 (WT2; see, e.g., U.S. Pat. No. 5,726,288).

The chromosomal region in which the KSE336 gene is located is involved in genomic imprinting, the phenomenon in which epigenetic modification of a specific parental chromosome in the gamete or zygote leads to monoallelic or differential expression of the two alleles of the gene in the offspring's somatic cells. An example of a disease localized to 11p15 and implicated in defective genomic imprinting is the Beckwith-Wiedemann syndrome (BWS). BWS is a disorder of prenatal overgrowth, cancer, and hypoglycemia (associated with pancreatic islet hyperplasia). It is known to be transmitted as an autosomal dominant trait, but also occasionally arises spontaneously. Two separate domains of imprinted genes appear to be involved in BWS. See, e.g., Lee et al., *Proc. Natl. Acad. Sci.*, 96:5203–5208, 1999; Maher and Reik, *J. Clin. Invest.*, 105:247–252, 2000; Feinberg, *J. Clin. Invest.*, 106:739–740, 2000. About half of patients with BWS showed loss of imprinting (LOI) with LIT1, but only 20% with IGF2 (Lee et al., *Proc. Natl. Acad. Sci.*, 96:5203–5208, 1999). Accordingly, nucleic acids of the present invention, including SNPs and other polymorphisms of it, can be use as probes to analyze whether a gene has been imprinted.

Activity

By the phrase "serine/threonine kinase activity," it is meant a catalytic activity in which a gamma phosphate from adenosine triphosphate (ATP) is transferred to a serine or threonine residue in a protein substrate. More generally, a "kinase activity" refers to the ability of an enzyme to catalyze the transfer of a phosphate from one molecule to another.

Kinase activity of KSE336, and biologically active fragments thereof, can be determined routinely using conventional assay methods. Kinase assays typically comprise the kinase enzyme, substrates, buffers, and components of a detection system. A typical kinase assay involves a reaction of a protein kinase sample with a peptide substrate and a gamma-labeled ATP, such as $^{32}$P-ATP. The resulting labeled phosphoprotein is then separated from the gamma-labeled ATP. Separation and detection of the phosphoprotein can be achieved through any suitable method. When a radioactive label is utilized, the labeled phosphoprotein can be separated from the unreacted gamma-$^{32}$P-ATP using an affinity membrane or gel electrophoresis, and then visualized on the gel using autoradiography.

Non-radioactive methods can also be used. Methods can utilize an antibody which recognizes the phosphorylated substrate, e.g., an anti-phosphoserine or anti-phosphothreonine antibody. For instance, kinase enzyme can incubated with a substrate in the presence of ATP and kinase buffer under conditions which are effective for the enzyme to phosphorylate the substrate. The reaction mixture can be separated, e.g., electrophoretically, and then phosphorylation of the substrate can be measured by Western blotting using an anti-phosphoserine or anti-phosphothreonine antibody. The antibody can be labeled with a detectable label, e.g., an enzyme, such as HRP, avidin or biotin, chemiluminescent reagents, etc. Other methods can utilize ELISA formats, affinity membrane separation, fluorescence polarization assays, luminescent assays, etc. Kinase assays are available commercially, e.g., Cell Signaling Corporation (e.g., p44/42 MAP Kinase Assay Kit), AUSA Universal Protein Kinase Assay Kit, ProMega (e.g., PepTag assays), SpinZyme colorimetric assays from Pierce, Calbiochem's ELISA-based kinase assays, Upstate Biotechnology's ELISA-based kits using chemiluminescent DuoLuX substrate from Vector Laboratories, PanVera's fluorescent polarization kits, etc.

For kinase assays, see also, e.g., Kemp et al., "Design and use of peptide substrates for protein kinases," *Methods in Enzymol.*, 200:121–34, 1991; Wang et al., "Identification of the major site of rat prolactin phosphorylation as serine 177," *J. Biol. Chem.*, 271:2462–9, 1996; Yasuda et al., "A synthetic peptide substrate for selective assay of protein kinase C," *Biochem. Biophys. Res. Comm.*, 166:1220–7, 1990; Gonzalez et al., "Use of the synthetic peptide neurogranin(28–43) as a selective protein kinase C substrate in assays of tissue homogenates," *Anal. Biochem.*, 215:184–9, 1993; Parker et al., "Development of high throughput screening assays using fluorescence polarization: nuclear receptor-ligand-binding and kinase/phosphatase assays," *J. Biomol. Screen.*, 5:77–88, April 2000. See, also., U.S. Pat. Nos. 6,203,994, 6,074,861, 6,066,462, 6,004,757, and 5,741,689.

When a serine/threonine kinase activity is to be detected, a suitable substrate comprises serine and threonine residues, e.g., Elk-1, MBP, histones, such as H3, protamine, protamine sulfate, neurogranin, glycogen synthase, and fragments and fusion proteins thereof, HMRSAMSGLHLVKRR (SEQ ID NO 15), LRRASLG (SEQ ID NO 16), etc. Originally, a consensus PKC phosphorylation motif was determined to be RXXS/TXRX, where X indicates any amino acid. Generally, PKCs prefer basic residues at positions -6,-4 and -2 to the Ser/Thr. cPKCs also preferred basic residues at +2, +3 and +4, whereas nPKC and aPKCs preferred hydrophobic residues at these positions. PKCmu deviates from this specificity, having an optimal motif which differs from other PKCs, with a strong selectivity for Leu at the -5 position. See, e.g., Toker, *Frontiers in Bioscience*, 3:d1134–1147, 1998. PKAs can be assayed according to, e.g., Davies et al., *Eur. J. Biochem.*, 186:123–128, 1989; Roskoski, *Methods Enymol.*, 99:3–6, 1983; Cob and Corbin, *Methods Enzymol.*, 159:202–208, 1988. Consensus sequences for KSE336 can be determined analogously.

Nucleic Acids

A mammalian polynucleotide, or fragment thereof, of the present invention is a polynucleotide having a nucleotide sequence obtainable from a natural source. It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines. Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc. A polynucleotide which "codes without interruption" refers to a polynucleotide having a continuous open reading frame ("ORF") as compared to an ORF which is interrupted by introns or other noncoding sequences.

Polynucleotides and polypeptides (including any part of KSE336) can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application. AJ006701 (SEQ ID NO 17) and AF020089 (SEQ ID NO 18) can be excluded from the present invention, e.g., KSE336, fragments thereof, wherein such fragment is not AJ006701 or AF020089.

As described herein, the phrase "an isolated polynucleotide which is SEQ ID NO," or "an isolated polynucleotide which is selected from SEQ ID NO," refers to an isolated nucleic acid molecule from which the recited sequence was derived (e.g., a cDNA derived from mRNA; cDNA derived from genomic DNA). Because of sequencing errors, typographical errors, etc., the actual naturally-occurring sequence may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube.

As explained in more detail below, a polynucleotide sequence of the invention can contain the complete sequence as shown in SEQ ID NO 1 and 2, degenerate sequences thereof, anti-sense, muteins thereof, genes comprising said sequences, full-length cDNAs comprising said sequences, complete genomic sequences, fragments thereof (e.g., SEQ ID NOS 3 and 4), homologs, primers, nucleic acid molecules which hybridize thereto, derivatives thereof, etc.

Genomic

The present invention also relates genomic DNA from which the polynucleotides of the present invention can be derived. A genomic DNA coding for a human, mouse, or other mammalian polynucleotide, can be obtained routinely, for example, by screening a genomic library (e.g., a YAC library) with a polynucleotide of the present invention, or by searching nucleotide databases, such as GenBank and EMBL, for matches. Promoter and other regulatory regions can be identified upstream of coding and expressed RNAs, and assayed routinely for activity, e.g., by joining to a reporter gene (e.g., CAT, GFP, alkaline phosphatase, luciferase, galatosidase). A promoter obtained from a brain and pancreas selective gene can be used, e.g., in gene therapy to obtain tissue-specific expression of a heterologous gene (e.g., coding for a therapeutic product or cytotoxin). Specific genomic promoter sequences are listed in Table 1.

Constructs

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, enzymatic, fluorescent, antibiotic resistance, and other functional or diagnostic peptides); coding sequences and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR54 0, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRMII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Hybridization

Polynucleotide hybridization, as discussed in more detail below, is useful in a variety of applications, including, in gene detection methods, for identifying mutations, for making mutations, to identify homologs in the same and different species, to identify related members of the same gene family, in diagnostic and prognostic assays, in therapeutic applications (e.g., where an antisense polynucleotide is used to inhibit expression), etc.

The ability of two single-stranded polynucleotide preparations to hybridize together is a measure of their nucleotide sequence complementarity, e.g., base-pairing between nucleotides, such as A-T, G-C, etc. The invention thus also relates to polynucleotides, and their complements, which hybridize to a polynucleotide comprising a nucleotide sequence as set forth in SEQ ID NOS 1–6 and genomic sequences thereof. A nucleotide sequence hybridizing to the latter sequence will have a complementary polynucleotide strand, or act as a template for one in the presence of a polymerase (i.e., an appropriate polynucleotide synthesizing enzyme). The present invention includes both strands of polynucleotide, e.g., a sense strand and an anti-sense strand.

Hybridization conditions can be chosen to select polynucleotides which have a desired amount of nucleotide complementarity with the nucleotide sequences set forth in SEQ ID NOS 1–6 and genomic sequences thereof. A polynucleotide capable of hybridizing to such sequence, preferably, possesses, e.g., about 70%, 75%, 80%, 85%, 87%, 90%, 92%, 95%, 97%, 99%, or 100% complementarity, between the sequences. The present invention particularly relates to polynucleotide sequences which hybridize to the nucleotide sequences set forth in SEQ ID NOS 1–6 or genomic sequences thereof, under low or high stringency conditions. These conditions can be used, e.g., to select corresponding homologs in non-human species.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6×SSC, 0.5% SDS, 100 μg/ml denatured salmon sperm DNA, 5× Denhardt's solution, and 50% formamide), at 22–68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology*, Chapter 6, Screening of Recombinant Libraries; Sambrook et al., *Molecular Cloning*, 1989, Chapter 9.

For instance, high stringency conditions can be achieved by incubating the blot overnight (e.g., at least 12 hours) with a long polynucleotide probe in a hybridization solution containing, e.g., about 5×SSC, 0.5% SDS, 100 μg/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Other non-limiting examples of high stringency conditions includes a final wash at 65° C. in aqueous buffer containing 30 mM NaCl and 0.5% SDS. Another example of high stringent conditions is hybridization in 7% SDS, 0.5M NaPO$_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

Hybridization can also be based on a calculation of melting temperature (Tm) of the hybrid formed between the probe and its target, as described in Sambrook et al.. Generally, the temperature Tm at which a short oligonucleotide (containing 18 nucleotides or fewer) will melt from its target sequence is given by the following equation: Tm=(number of A's and T's)×2° C.+(number of C's and G's)×4° C. For longer molecules, Tm=81.5+16.6 log$_{10}$[Na$^+$]+0.41 (%GC)−600/N where [Na$^+$] is the molar concentration of sodium ions, %GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 90%, 95%, or 97%, nucleotide complementarity between the probe (e.g., a short polynucleotide of SEQ ID NOS 1–6 or genomic sequences thereof) and a target polynucleotide.

Other homologs of polynucleotides of the present invention can be obtained from mammalian and non-mammalian sources according to various methods. For example, hybridization with a polynucleotide can be employed to select homologs, e.g., as described in Sambrook et al., *Molecular Cloning*, Chapter 11, 1989. Such homologs can have varying amounts of nucleotide and amino acid sequence identity and similarity to such polynucleotides of the present invention. Mammalian organisms include, e.g., mice, rats, monkeys, pigs, cows, etc. Non-mammalian organisms include, e.g., vertebrates, invertebrates, zebra fish, chicken, Drosophila, *C. elegans*, Xenopus, yeast such as *S. pombe, S. cerevisiae*, roundworms, prokaryotes, plants, Arabidopsis, artemia, viruses, etc. The degree of nucleotide sequence identity between human and mouse can be about, e.g. 70% or more, 85% or more for open reading frames, etc.

Alignment

Alignments can be accomplished by using any effective algorithm. For pairwise alignments of DNA sequences, the methods described by Wilbur-Lipman (e.g., Wilbur and Lipman, *Proc. Natl. Acad. Sci.*, 80:726–730, 1983) or Martinez/Needleman-Wunsch (e.g., Martinez, *Nucleic Acid Res.*, 11:4629–4634, 1983) can be used. For instance, if the Martinez/Needleman-Wunsch DNA alignment is applied, the minimum match can be set at 9, gap penalty at 1.10, and gap length penalty at 0.33. The results can be calculated as a similarity index, equal to the sum of the matching residues divided by the sum of all residues and gap characters, and then multiplied by 100 to express as a percent. Similarity index for related genes at the nucleotide level in accordance with the present invention can be greater than 70%, 80%, 85%, 90%, 95%, 99%, or more. Pairs of protein sequences can be aligned by the Lipman-Pearson method (e.g., Lipman and Pearson, *Science*, 227:1435–1441, 1985) with k-tuple set at 2, gap penalty set at 4, and gap length penalty set at 12. Results can be expressed as percent similarity index, where related genes at the amino acid level in accordance with the present invention can be greater than 65%, 70%, 75%, 80%, 85%, 90%, 95%, 99%, or more. Various commercial and free sources of alignment programs are available, e.g., MegAlign by DNA Star, BLAST (National Center for Biotechnology Information), BCM (Baylor College of Medicine) Launcher, etc.

Percent sequence identity can also be determined by other conventional methods, e.g., as described in Altschul et al., *Bull. Math. Bio.* 48:603–616, 1986 and Henikoff and Henikoff, *Proc. Natl. Acad. Sci. USA* 89:10915–10919, 1992.

Specific Polynucleotide Probes

A polynucleotide of the present invention can comprise any continuous nucleotide sequence of SEQ ID NOS 1–6, sequences which share sequence identity thereto, or complements thereof. The term "probe" refers to any substance that can be used to detect, identify, isolate, etc., another substance. A polynucleotide probe is comprised of nucleic acid can be used to detect, identify, etc., other nucleic acids, such as DNA and RNA.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7–2000 nucleotides, 7–1000, 8–700, 8–600, 8–500, 8–400, 8–300, 8–150, 8–75, 7–50, 10–25, 14–16, at least about 8, at least about 10, at least about 15, at least about 25 etc. The polynucleotides can have non-naturally-occurring nucleotides, e.g., inosine, AZT, 3TC, etc. The polynucleotides can have 100% sequence identity or complementarity to a sequence of SEQ ID NOS 1–6, or it can have mismatches or nucleotide substitutions, e.g., 1, 2, 3, 4, or 5 substitutions. The probes can be single-stranded or double-stranded.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for KSE336, e.g., comprising a forward and reverse primer effective in PCR. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample. It is specific in the sense that it can be used to detect polynucleotides above background noise ("non-specific binding"). A specific sequence is a defined order of nucleotides which occurs in the polynucleotide, e.g., in the nucleotide sequences of SEQ ID NOS 1–6. A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human or mouse polynucleotide, in a sample comprising a mixture of polynucleotides, e.g., on a Northern blot. Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

A polynucleotide probe, especially one that is specific to a polynucleotide of the present invention, can be used in gene detection and hybridization methods as already described. In one embodiment, a specific polynucleotide probe can be used to detect whether a particular tissue or cell-type is present in a target sample. To carry out such a method, a selective polynucleotide can be chosen which is characteristic of the desired target tissue. Such polynucleotide is preferably chosen so that it is expressed or displayed in the target tissue, but not in other tissues which are present in the sample. For instance, if detection of brain and pancreas is desired, it may not matter whether the selective polynucleotide is expressed in other tissues, as long as it is not expressed in cells normally present in blood, e.g., peripheral blood mononuclear cells. Starting from the selective polynucleotide, a specific polynucleotide probe can be designed which hybridizes (if hybridization is the basis of the assay) under the hybridization conditions to the selective polynucleotide, whereby the presence of the selective polynucleotide can be determined.

Probes which are specific for polynucleotides of the present invention can also be prepared using involve transcription-based systems, e.g., incorporating an RNA polymerase promoter into a selective polynucleotide of the present invention, and then transcribing anti-sense RNA using the polynucleotide as a template. See, e.g., U.S. Pat. No. 5,545,522.

Polynucleotide Composition

A polynucleotide according to the present invention can comprise, e.g., DNA, RNA, synthetic polynucleotide, peptide polynucleotide, modified nucleotides, dsDNA, ssDNA, ssRNA, dsRNA, and mixtures thereof. A polynucleotide can be single- or double-stranded, triplex, DNA:RNA, duplexes, comprise hairpins, and other secondary structures, etc. Nucleotides comprising a polynucleotide can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

Various modifications can be made to the polynucleotides, such as attaching detectable markers (avidin, biotin, radioactive elements, fluorescent tags and dyes, energy transfer labels, energy-emitting labels, binding partners, etc.) or moieties which improve hybridization, detection, and/or stability. The polynucleotides can also be attached to solid supports, e.g., nitrocellulose, magnetic or paramagnetic microspheres (e.g., as described in U.S. Pat. Nos. 5,411,863; 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967, 5,476,925, and 5,478,893.

Polynucleotide according to the present invention can be labeled according to any desired method. The polynucleotide can be labeled using radioactive tracers such as $^{32}P$, $^{35}S$, $^3H$, or $^{14}C$, to mention some commonly used tracers. The radioactive labeling can be carried out according to any method, such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a polynucleotide of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

Nucleic Acid Detection Methods

Another aspect of the present invention relates to methods and processes for detecting KSE336. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., Science, 241:53, 1988; U.S. Pat. Nos. 4,683,195, 4,683,202, and 6,040,166; PCR Protocols: A Guide to Methods and Applications, Inis et al., eds., Academic Press, New York, 1990), reverse transcriptase polymerase chain reaction ("RT-PCR"), anchored PCR, rapid amplification of cDNA ends ("RACE") (e.g., Schaefer in Gene Cloning and Analysis: Current Innovations, Pages 99–115, 1997), ligase chain reaction ("LCR") (EP 320 308), one-sided PCR (Ohara et al., Proc. Natl. Acad. Sci., 86:5673–5677, 1989), indexing methods (e.g., U.S. Pat. No. 5,508,169), in situ hybridization, differential display (e.g., Liang et al., Nucl. Acid. Res., 21:3269–3275, 1993; U.S. Pat. Nos. 5,262,311, 5,599,672 and 5,965,409; WO97/18454; Prashar and Weissman, Proc. Natl. Acad. Sci., 93:659–663, and U.S. Pat. Nos. 6,010,850 and 5,712,126; Welsh et al., Nucleic Acid Res., 20:4965–4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., Proc. Natl. Acad, Sci., 88:7276–7280, 1991; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, Nature Biotech., 14:303–309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., Methods Mol. & Cell. Biol. 2, 17–25, 1990; Eberwine et al., 1992, Proc. Natl. Acad. Sci., 89, 3010–3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

Polynucleotides can be used in wide range of methods and compositions, including for detecting, diagnosing, staging, grading, assessing, prognosticating, etc. diseases and disorders associated with KSE336, for monitoring or assessing therapeutic and/or preventative measures, in ordered arrays, etc. Any method of detecting genes and polynucleotides of SEQ ID NOS 1–6 can be used; certainly, the present invention is not to be limited how such methods are implemented.

Along these lines, the present invention relates to methods of detecting KSE336 in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample, wherein said probe is a polynucleotide which is SEQ ID NOS 1–6, a polynucleotide having, e.g., about 70%, 80%, 85%, 90%, 95%, 99%, or more sequence identity thereto, effective or specific fragments thereof, or complements thereto. The detection method can be applied to any sample, e.g., cultured primary, secondary, or established cell lines, tissue biopsy, blood, urine, stool, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of a polynucleotide set forth in SEQ ID NOS 1–6 is desired, a probe can be selected which can hybridize to such target gene under high stringent conditions, without significant hybridization to other genes in the sample. To detect homologs of a polynucleotide set forth in SEQ ID NOS 1 and 2, the effective hybridization conditions can be less stringent, and/or the probe can comprise codon degeneracy, such that a homolog is detected in the sample.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain cancer cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

Methods of Identifying Polymorphisms, Mutations, etc., of KSE336

Polynucleotides of the present invention can also be utilized to identify mutant alleles, SNPs, gene rearrangements and modifications, and other polymorphisms of the wild-type gene. Mutant alleles, polymorphisms, SNPs, etc., can be identified and isolated from cancers that are known, or suspected to have, a genetic component. Identification of such genes can be carried out routinely (see, above for more guidance), e.g., using PCR, hybridization techniques, direct sequencing, mismatch reactions (see, e.g., above), RFLP analysis, SSCP (e.g., Orita et al., *Proc. Natl. Acad. Sci.,* 86:2766, 1992), etc., where a polynucleotide having a sequence selected from SEQ ID NOS 1 and 2 is used as a probe. The selected mutant alleles, SNPs, polymorphisms, etc., can be used diagnostically to determine whether a subject has, or is susceptible to a disorder associated with KSE336, as well as to design therapies and predict the outcome of the disorder. Methods involve, e.g., diagnosing a disorder associated with KSE336, comprising, detecting the presence of a mutation in a gene represented by a polynucleotide selected from SEQ ID NOS 1 and 2. The detecting can be carried out by any effective method, e.g., obtaining cells from a subject, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Polynucleotides can also be used to test for mutations, SNPs, polymorphisms, etc., e.g., using mismatch DNA repair technology as described in U.S. Pat. Nos. 5,683,877; 5,656,430; Wu et al., *Proc. Natl. Acad. Sci.,* 89:8779–8783, 1992.

The present invention also relates to methods of detecting polymorphisms in KSE336, comprising, e.g., comparing the structure of: genomic DNA comprising all or part of KSE336, mRNA comprising all or part of KSE336, cDNA comprising all or part of KSE336, or a polypeptide comprising all or part of KSE336, with the structure of KSE336 set forth in SEQ ID NOS 1–6. The methods can be carried out on a sample from any source, e.g., cells, tissues, body fluids, blood, urine, stool, hair, egg, sperm, etc.

These methods can be implemented in many different ways. For example, "comparing the structure" steps include, but are not limited to, comparing restriction maps, nucleotide sequences, amino acid sequences, RFLPs, Dnase sites, DNA methylation fingerprints (e.g., U.S. Pat. No. 6,214,556), protein cleavage sites, molecular weights, electrophoretic mobilities, charges, ion mobility, etc., between a standard KSE336 and a test KSE336. The term "structure" can refer to any physical characteristics or configurations which can be used to distinguish between nucleic acids and polypeptides. The methods and instruments used to accomplish the comparing step depends upon the physical characteristics which are to be compared. Thus, various techniques are contemplated, including, e.g., sequencing machines (both amino acid and polynucleotide), electrophoresis, mass spectrometer (U.S. Pat. Nos. 6,093,541, 6,002,127), liquid chromatography, HPLC, etc.

To carry out such methods, "all or part" of the gene or polypeptide can be compared. For example, if nucleotide sequencing is utilized, the entire gene can be sequenced, including promoter, introns, and exons, or only parts of it can be sequenced and compared, e.g., exon 1, exon 2, etc.

Mutagenesis

Mutated polynucleotide sequences of the present invention are useful for various purposes, e.g., to create mutations of the polypeptides they encode, to identify functional regions of genomic DNA, to produce probes for screening libraries, etc. Mutagenesis can be carried out routinely according to any effective method, e.g., oligonucleotide-directed (Smith, M., Ann. Rev. Genet. 19:423–463, 1985), degenerate oligonucleotide-directed (Hill et al., Method Enzymology, 155:558–568, 1987), region-specific (Myers et al., Science, 229:242–246, 1985; Derbyshire et al., Gene, 46:145, 1986; Ner et al., DNA, 7:127, 1988), linker-scanning (McKnight and Kingsbury, Science, 217:316–324, 1982), directed using PCR, recursive ensemble mutagenesis (Arkin and Yourvan, Proc. Natl. Acad. Sci., 89:7811–7815, 1992), random mutagenesis (e.g., U.S. Pat. Nos. 5,096,815; 5,198,346; and 5,223,409), site-directed mutagenesis (e.g., Walder et al., Gene, 42:133, 1986; Bauer et al., Gene, 37:73, 1985; Craik, Bio Techniques, January 1985, 12–19; Smith et al., Genetic Engineering: Principles and Methods, Plenum Press, 1981), phage display (e.g., Lowman et al., Biochem. 30:10832–10837, 1991; Ladner et al., U.S. Pat. No. 5,223,409; Huse, WIPO Publication WO 92/06204), etc. Desired sequences can also be produced by the assembly of target sequences using mutually priming oligonucleotides (Uhlmann, Gene, 71:29–40, 1988). For directed mutagenesis methods, analysis of the three-dimensional structure of the KSE336 polypeptide can be used to guide and facilitate making mutants which effect polypeptide activity. Sites of substrate-enzyme interaction or other biological activities can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et al., FEBS Lett. 309:59–64, 1992.

In addition, libraries of KSE336 and fragments thereof can be used for screening and selection of KSE336 variants. For instance, a library of coding sequences can be generated by treating a double-stranded DNA with a nuclease under conditions where the nicking occurs, e.g., only once per molecule, denaturing the double-stranded DNA, renaturing it to for double-stranded DNA that can include sense/antisense pairs from different nicked products, removing single-stranded portions from reformed duplexes by treatment with S1 nuclease, and ligating the resulting DNAs into an expression vecore. By this method, expression libraries can be made comprising "mutagenized" KSE336. The entire coding sequence or parts thereof can be used.

Polynucleotide expression, polypeptides produced thereby, and specific-binding partners thereto.

A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., COS, CVI, BHK, CHO, HeLa, LTK, NIH 3T3, CNS neural stem cells (e.g., U.S. Pat. No. 6,103,530), IMR-32, A172 (ATCC CRL-1620), T98G (ATCC CRL-1690), CCF-STTG1 (ATCC CRL-1718), DBTRG-05MG (ATCC CRL-2020), PFSK-1 (ATCC CRL-2060), SK-N-AS and other SK cell lines (ATCC CRL-2137), CHP-212 (ATCC CRL-2273), RG2 (ATCC CRL-2433), HCN-2 (ATCC CRL-10742), U-87 MG and other U MG cell lines (ATCC HTB-14), D283 Med (ATCC HTB-185), PC12, Neuro-2a (ATCC CCL-131), insulinoma cell lines, INS-H1, MIN6N8, RIN-5AH, RIN-A12, RINm5F, capan-1, capan-2, MIA PaCa-2 (ATCC CRL-1420), PANC-1 (ATCC CRL-1469), AsPC-1 (ATCC CRL-1682), SU-86.86 (ATCC CRL-1837), CFPAC-1 (ATCC CRL-1918), HPAF-II (ATCC CRL-1937), TGP61 (ATCC CRL-2135) and other TGP lines, SW 1990 (ATCC CRL-2172), Mpanc-96 (ATCC CRL-2380), MS1 VEGF (ATCC CRL-2460), Beta-TC-6 (ATCC CRL-11506), LTPA (ATCC CRL-2389), 266-6 (ATCC CRL-2151), MS1 (ATCC CRL-2779), SVR (ATCC CRL-2280), NIT-2 (ATCC CRL-2364), alphaTC1 Clone 9 (ATCC CRL-2350), ATCC CRL-1492, BxPC-3 (ATCC CRL-1687), HPAC (ATCC CRL-2119), U.S. Pat. Nos. 6,110,743, 5,928,942, 5,888,816, 5,888,705, and 5,723,333, etc., insect cells, such as Sf9 (S. frugipeda) and Drosophila, bacteria, such as E. coli, Streptococcus, bacillus, yeast, such as Sacharomyces, S. cerevisiae, fungal cells, plant cells, embryonic or adult stem cells (e.g., mammalian, such as mouse or human), pluripotent cells, etc.

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., Polynucleotide Res., 12(18):7035–7056, 1984; Dunn and Studier. J. Mol. Bio., 166:477–435, 1984; U.S. Pat. No. 5,891,636; Studier et al., Gene Expression Technology, Methods in Enzymology, 85:60–89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, e.g., as set forth in SEQ ID NOS 1 and 2, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6xHis, maltose binding protein, chitinase, etc) and then purify by anti-tag antibody-conjugated affinity chromatography.

The present invention also relates to antibodies, and other specific-binding partners, which are specific for polypeptides encoded by polynucleotides of the present invention, e.g., KSE336. Antibodies, e.g., polyclonal, monoclonal, recombinant, chimeric, humanized, single-chain, Fab, and fragments thereof, can be prepared according to any desired method. See, also, screening recombinant immunoglobulin libraries (e.g., Orlandi et al., *Proc. Natl. Acad. Sci.,* 86:3833–3837, 1989; Huse et al., *Science,* 256:1275–1281, 1989); in vitro stimulation of lymphocyte populations; Winter and Milstein, *Nature,* 349: 293–299, 1991. The antibodies can be IgM, IgG, subtypes, IgG2a, IgG1, etc. Antibodies, and immune responses, can also be generated by administering naked DNA See, e.g., U.S. Pat. Nos. 5,703,055; 5,589,466; 5,580,859. Antibodies can be used from any source, including, goat, rabbit, mouse, chicken (e.g., IgY; see, Duan, WO/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA. antibodies can be prepared against specific epitopes or domains of KSE336, e.g., SEQ ID NO 4. The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, in U.S. Pat. No. 6,054,297, Jones et al., Nature 321:522 (1986); Riechmann et al., Nature 332:323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in *E. coli* of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab').sub.2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisoiihoff et al., Arch. Biochem. Biophys. 89:230 (1960); Porter, Biochem. J. 73:119 (1959); Edelman etal, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of $V_H$ and $V_L$ chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising nucleic acid sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird etal., Science 242:423–426 (1988); Ladner et al., U.S. Pat. No. 4,946,778; Pack et al., Bio/Technology 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains.

Antibodies which bind to KSE336 polypeptides of the present invention can be prepared using an intact polypeptide or fragments containing small peptides of interest as the immunizing antigen. For example, it may be desirable to produce antibodies that specifically bind to the N- or C-terminal domains of KSE336. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

Anti-idiotype technology can also be used to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Detecting Polypeptides

Polypeptides coded for by KSE336 of the present invention can be detected, visualized, determined, quantitated, etc. according to any effective method. useful methods include, e.g., but are not limited to, immunoassays, RIA (radioimmunoassay), ELISA, (enzyme-linked-immunosorbent assay), immunoflourescence, flow cytometry, histology, electron microscopy, light microscopy, in situ assays, immunoprecipitation, Western blot, etc.

Immunoassays may be carried in liquid or on biological support. For instance, a sample (e.g., blood, stool, urine, cells, tissue, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled KSE336 specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads.

One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, .alalpha.-glycerophosphate, dehydrogenase, triose phosphate isomerase, horseradish peroxidase, alkaline phosphatase, asparaginase, glucose oxidase, beta.-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect KSE336 peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoeryhrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Diagnostic

The present invention also relates to methods and compositions for diagnosing a brain or pancreas disorder, or determining whether a subject is susceptible to such a disorder, using polynucleotides, polypeptides, and specific-binding partners of the present invention to detect, assess, determine, etc., KSE336. In such methods, the gene can serve as a marker for the disorder, e.g., where the gene, when mutant, is a direct cause of the disorder; where the gene is affected by another gene(s) which is directly responsible for the disorder, e.g., when the gene is part of the same signaling pathway as the directly responsible gene; and, where the gene is chromosomally linked to the gene(s) directly responsible for the disorder, and segregates with it. Many other situations are possible. To detect, assess, determine, etc., a probe specific for the gene can be employed as described above and below. Any method of detecting and/or assessing the gene can be used, including detecting expression of the gene using polynucleotides, antibodies, or other specific-binding partners.

The present invention relates to methods of diagnosing a disorder associated with a disorder of KSE336, or determining whether a subject is susceptible to such a disorder, comprising, e.g., assessing the expression of KSE336 in a tissue sample comprising tissue or cells suspected of having the disorder (e.g., where the sample comprises brain and pancreas). The phrase "diagnosing" indicates that it is determined whether the sample has the disorder. A "disorder" means, e.g., any abnormal condition as in a disease or malady. "Determining a subject's susceptibility to a disease or disorder" indicates that the subject is assessed for whether s/he is predisposed to get such a disease or disorder, where the predisposition is indicated by abnormal expression of the gene (e.g., gene mutation, gene expression pattern is not normal, etc.). Predisposition or susceptibility to a disease may result when a such disease is influenced by epigenetic, environmental, etc., factors.

By the phrase "assessing expression of KSE336," it is meant that the functional status of the gene is evaluated. This includes, but is not limited to, measuring expression levels of said gene, determining the genomic structure of said gene, determining the mRNA structure of transcripts from said gene, or measuring the expression levels of polypeptide coded for by said gene. Thus, the term "assessing expression" includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a normal gene, e.g., a gene which is not associated with the disorder. The nature of the comparison can be determined routinely, depending upon how the assessing is accomplished. If, for example, the mRNA levels of a sample is detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Assessing the effects of therapeutic and preventative interventions (e.g., administration of a drug, chemotherapy, radiation, etc.) on brain and pancreas disorders is a major effort in drug discovery, clinical medicine, and pharmacogenomics. The evaluation of therapeutic and preventative measures, whether experimental or already in clinical use, has broad applicability, e.g., in clinical trials, for monitoring the status of a patient, for analyzing and assessing animal models, and in any scenario involving cancer treatment and prevention. Analyzing the expression profiles of polynucleotides of the present invention can be utilized as a parameter by which interventions are judged and measured. Treatment of a disorder can change the expression profile in some manner which is prognostic or indicative of the drug's effect on it. Changes in the profile can indicate, e.g., drug toxicity, return to a normal level, etc. Accordingly, the present invention also relates to methods of monitoring or assessing a therapeutic or preventative measure (e.g., chemotherapy, radiation, anti-neoplastic drugs, antibodies, etc.) in a subject having a brain and pancreas disorder, or, susceptible to such a disorder, comprising, e.g., detecting the expression levels of KSE336. A subject can be a cell-based assay system, non-human animal model, human patient, etc. Detecting can be accomplished as described for the methods above and below. By "therapeutic or preventative intervention," it is meant, e.g., a drug administered to a patient, surgery, radiation, chemotherapy, and other measures taken to prevent, treat, or diagnose a disorder.

Expression can be assessed in any sample comprising any tissue or cell type, body fluid, etc., as discussed for other methods of the present invention, including cells from brain and pancreas can be used, or cells derived from brain and pancreas. By the phrase "cells derived from brain and pancreas," it is meant that the derived cells originate from brain and pancreas, e.g., when metastasis from a primary tumor site has occurred, when a progenitor-type or pluripotent cell gives rise to other cells, etc.

Identifying Agent Methods

The present invention also relates to methods of identifying agents that modulate the expression of KSE336 expressed in brain and pancreas cells, comprising, in any effective order, one or more of the following steps, e.g., contacting a cell population with a test agent under conditions effective for said test agent to modulate the expression of KSE336 in said cell population, and determining whether said test agent modulates said KSE336. An agent can modulate expression of KSE336 at any level, including transcription, translation, and/or perdurance of the nucleic acid or polypeptide (e.g., degradation, stability, etc.) product in the cell.

Contacting the cell population with the test agent can be accomplished by any suitable method and/or means that places the agent in a position to functionally control expression of the KSE336 present in cells within the population. Functional control indicates that the agent can exert its physiological effect on the cell through whatever mechanism it works. The choice of the method and/or means can depend upon the nature of the agent and the condition and type of the cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to the cells, it can be determined whether the test agent modulates KSE336 expression. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold, etc. To modulate KSE336 expression means, e.g., that the test agent has an effect on its expression, e.g., to effect the amount of transcription, to effect RNA splicing, to effect translation of the RNA into polypeptide, to effect RNA or polypeptide stability, to effect polyadenylation or other processing of the RNA, to effect post-transcriptional or post-translational processing, etc.

A test agent can be of any molecular composition, e.g., chemical compounds, biomolecules, such as polypeptides, lipids, nucleic acids (e.g., antisense to a polynucleotide sequence selected from SEQ ID NOS 1 and 2), carbohydrates, antibodies, ribozymes, double-stranded RNA, etc. For example, if a gene to be modulated is a cell-surface molecule, a test agent can be an antibody that specifically recognizes it and leads to some effect on its expression. An antibody can cause the polypeptide to be internalized, leading to its down regulation on the surface of the cell. Such an effect does not have to be permanent, but can require the presence of the antibody to continue the down-regulatory effect. Antisense KSE336 can also be used as test agents to modulate gene expression.

Markers

The polynucleotides of the present invention can be used with other markers, especially brain and pancreas markers, to identity, detect, stage, diagnosis, determine, prognosticate, treat, etc., tissue, diseases and conditions, etc, of the brain and pancreas. Markers can be polynucleotides, polypeptides, antibodies, ligands, specific binding partners, etc. The targets for such markers include, but are not limited genes and polypeptides that are selective for cell types present in the brain and pancreas. Specific targets include, The targets for such markers include, but are not limited, presenilins, genes and polypeptides in the pathways for neurotransmitter synthesis, receptor, metabolism, etc., (e.g., serotonin, MAO, dopamine, norephinephrine, nitric oxide, etc.), apolipoprotein A, APP, neuron-specific enolase (NSE), glial fibrillary acidic protein (GFAP), S100, GAP-43, neuron-specific beta-III tubulin, Stac (neuron-specific protein with an SH3 domain, e.g., *Genomics*, 47:140–2, 1998), myelin basic protein, etc. vimentin, lannotti et al., *Genomics*, 46:520–524, 1997), ZG-46p (Chen et al., *Eur. J. Cell. Biol.*, 3:205–214, 1997), calretinin, islet amyloid pancreatic polypeptide, SLC26A6 (e.g., on apical surface of pancreatic ductal cells), reg/PSP mutligene family (e.g., Unno et al. *J. Biol. Chem.*, 268:15974–82, 1993), pancreatitis-associated proteins (e.g., Dusetti et al., *Genomics*, 19:108–114, 1994), PANC1A and PANC1B (U.S. Pat. No. 5,840,870), antibodies (e.g., U.S. Pat. No. 5,888,813 and 5,622,837), INGAP (U.S. Pat. No. 5,840,531), insulin, glucagons, etc.

Therapeutics

Selective polynucleotides, polypeptides, and specific-binding partners thereto, can be utilized in therapeutic applications, especially to treat diseases and conditions of brain and pancreas. Useful methods include, but are not limited to, immunotherapy (e.g., using specific-binding partners to polypeptides), vaccination (e.g., using a selective polypeptide or a naked DNA encoding such polypeptide), protein or polypeptide replacement therapy, gene therapy (e.g., germ-line correction, antisense), etc.

Various immunotherapeutic approaches can be used. For instance, unlabeled antibody that specifically recognizes a tissue-specific antigen can be used to stimulate the body to destroy or attack the cancer, to cause down-regulation, to produce complement-mediated lysis, to inhibit cell growth, etc., of target cells which display the antigen, e.g., analogously to how c-erbB-2 antibodies are used to treat breast cancer. In addition, antibody can be labeled or conjugated to enhance its deleterious effect, e.g., with radionuclides and other energy emitting entitities, toxins, such as ricin, exotoxin A (ETA), and diphtheria, cytotoxic or cytostatic agents, immunomodulators, chemotherapeutic agents, etc. See, e.g., U.S. Pat. No. 6,107,090.

An antibody or other specific-binding partner can be conjugated to a second molecule, such as a cytotoxic agent, and used for targeting the second molecule to a tissue-antigen positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). Examples of cytotoxic agents include, but are not limited to, antimetabolites, alkylating agents, anthracyclines, antibiotics, anti-mitotic agents, radioisotopes and chemotherapeutic agents. Further examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, 1-dehydrotestosterone, diptheria toxin, Pseudomonas exotoxin (PE) A, PE40, abrin, elongation factor-2 and glucocorticoid. Techniques for conjugating therapeutic agents to antibodies are well.

In addition to immunotherapy, polynucleotides and polypeptides can be used as targets for non-immunotherapeutic applications, e.g., using compounds which interfere with function, expression (e.g., antisense as a therapeutic agent), assembly, etc. RNA interference can be used in vitro and in vivo to silence KSE336 when its expression contributes to a disease (but also for other purposes, e.g., to identify the gene's function to change a developmental pathway of a cell, etc.). See, e.g., Sharp and Zamore, Science, 287:2431–2433, 2001; Grishok et al., Science, 287:2494, 2001.

Delivery of therapeutic agents can be achieved according to any effective method, including, liposomes, viruses, plasmid vectors, bacterial delivery systems, orally, systemically, etc.

In addition to therapeutics, per se, the present invention also relates to methods of treating a disease of the brain, pancreas, or progenitor tissue thereof showing altered expression of KSE336, comprising, e.g., administering to a subject in need thereof a therapeutic agent which is effective for regulating expression of said KSE336 and/or which is effective in treating said disease. The term "treating" is used conventionally, e.g., the management or care of a subject for the purpose of combating, alleviating, reducing, relieving, improving the condition of, etc., of a disease or disorder. Various disease can be treated, including, but not limited to, astrocytoma, meningioma, pancreatic adenocarcinoma, insulin-dependent diabetes mellitus 2 (IDDM2), helicoid peripapillary chorioretinal degeneration (also known as atrophia areata), Beckwith-Wiedemann syndrome, and congenital hyperinsulinism.

By the phrase "altered expression," it is meant that the disease is associated with a mutation in the gene, or any modification to the gene (or corresponding product) which affects its normal function. Thus, expression of KSE336 refers to, e.g., transcription, translation, splicing, stability of the mRNA or protein product, activity of the gene product, differential expression, etc.

Any agent which "treats" the disease can be used. Such an agent can be one which regulates the expression of the KSE336. Expression refers to the same acts already mentioned, e.g. transcription, translation, splicing, stability of the mRNA or protein product, activity of the gene product, differential expression, etc. For instance, if the condition was a result of a complete deficiency of the gene product, administration of gene product to a patient would be said to treat the disease and regulate the gene's expression. Many other possible situations are possible, e.g., where the gene is aberrantly expressed, and the therapeutic agent regulates the aberrant expression by restoring its normal expression pattern.

Antisense

Antisense polynucleotide (e.g., RNA) can also be prepared from a polynucleotide according to the present invention, preferably an anti-sense to a sequence of SEQ ID NO 1 and 2. Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An antisense polynucleotides can be operably linked to an expression control sequence. A total length of about 35 bp can be used in cell culture with cationic liposomes to facilitate cellular uptake, but for in vivo use, preferably shorter oligonucleotides are administered, e.g. 25 nucleotides.

Antisense polynucleotides can comprise modified, nonnaturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121,437; 5,218,103 (e.g., nucleoside thiophosphoramidites); U.S. Pat. No. 4,973,679; Sproat et al., "2'-O-Methyloligoribonucleotides: synthesis and applications," Oligonucleotides and Analogs A Practical Approach, Eckstein (ed.), IRL Press, Oxford, 1991, 49–86; Iribarren et al., "2'O-Alkyl Oligoribonucleotides as Antisense Probes," Proc. Natl. Acad. Sci. USA, 1990, 87, 7747–7751; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629–2635.

Arrays

The present invention also relates to an ordered array of polynucleotide probes and specific-binding partners (e.g., antibodies) for detecting the expression of KSE336 in a sample, comprising, one or more polynucleotide probes or specific binding partners associated with a solid support, wherein each probe is specific for KSE336, and the probes comprise a nucleotide sequence of SEQ ID NO 1 and 2 which is specific for said gene, a nucleotide sequence having sequence identity to SEQ ID NO 1 and 2 which is specific for said gene or polynucleotide, or complements thereto, or a specific-binding partner which is specific for KSE336.

The phrase "ordered array" indicates that the probes are arranged in an identifiable or position-addressable pattern, e.g., such as the arrays disclosed in U.S. Pat. Nos. 6,156,501, 6,077,673, 6,054,270, 5,723,320, 5,700,637, WO0991971 1, WO00023803. The probes are associated with the solid support in any effective way. For instance, the probes can be bound to the solid support, either by polymerizing the probes on the substrate, or by attaching a probe to the substrate. Association can be, covalent, electrostatic, noncovalent, hydrophobic, hydrophilic, noncovalent, coordination, adsorbed, absorbed, polar, etc. When fibers or hollow filaments are utilized for the array, the probes can fill the hollow orifice, be absorbed into the solid filament, be attached to the surface of the orifice, etc. Probes can be of any effective size, sequence identity, composition, etc., as already discussed.

Ordered arrays can further comprise polynucleotide probes or specific-binding partners which are specific for other genes, including genes specific for brain and pancreas or disorders associated with brain and pancreas.

Transgenic Animals

The present invention also relates to transgenic animals comprising KSE336 genes. Such genes, as discussed in more detail below, include, but are not limited to, functionally-disrupted genes, mutated genes, ectopically or selectively-expressed genes, inducible or regulatable genes, etc. These transgenic animals can be produced according to any suitable technique or method, including homologous recombination, mutagenesis (e.g., ENU, Rathkolb et al., Exp. Physiol., 85(6):635–644, 2000), and the tetracycline-regulated gene expression system (e.g., U.S. Pat. No. 6,242,667). The term "gene" as used herein includes any part of a gene, i.e., regulatory sequences, promoters, enhancers, exons, introns, coding sequences, etc. The KSE336 nucleic acid present in the construct or transgene can be naturally-occurring wild-type, polymorphic, or mutated.

Along these lines, polynucleotides of the present invention can be used to create transgenic animals, e.g. a non-human animal, comprising at least one cell whose genome comprises a functional disruption of KSE336. By the phrases "functional disruption" or "functionally disrupted," it is meant that the gene does not express a biologically-active product. It can be substantially deficient in at least one functional activity coded for by the gene. Expression of a polypeptide can be substantially absent, i.e., essentially undetectable amounts are made. However, polypeptide can also be made, but which is deficient in activity, e.g., where only an amino-terminal portion of the gene product is produced.

The transgenic animal can comprise one or more cells. When substantially all its cells contain the engineered gene, it can be referred to as a transgenic animal "whose genome comprises" the engineered gene. This indicates that the endogenous gene loci of the animal has been modified and substantially all cells contain such modification.

Functional disruption of the gene can be accomplished in any effective way, including, e.g., introduction of a stop codon into any part of the coding sequence such that the resulting polypeptide is biologically inactive (e.g., because it lacks a catalytic domain, a ligand binding domain, etc.), introduction of a mutation into a promoter or other regulatory sequence that is effective to turn it off, or reduce transcription of the gene, insertion of an exogenous sequence into the gene which inactivates it (e.g., which disrupts the production of a biologically-active polypeptide or which disrupts the promoter or other transcriptional machinery), deletion of sequences from the KSE336 gene, etc. Examples of transgenic animals having functionally disrupted genes are well known, e.g., as described in U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. A transgenic animal which comprises the functional disruption can also be referred to as a "knock-out" animal, since the biological activity of its KSE336 genes has been "knocked-out." Knock-outs can be homozygous or heterozygous.

For creating functional disrupted genes, and other gene mutations, homologous recombination technology is of special interest since it allows specific regions of the genome to be targeted. Using homologous recombination methods, genes can be specifically-inactivated, specific mutations can be introduced, and exogenous sequences can be introduced at specific sites. These methods are well known in the art, e.g., as described in the patents above. See, also, Robertson, Biol. Reproduc., 44(2):238–245, 1991. Generally, the genetic engineering is performed in an embryonic stem (ES) cell, or other pluripotent cell line (e.g., adult stem cells, EG cells), and that genetically-modified cell (or nucleus) is used to create a whole organism. Nuclear transfer can be used in combination with homologous recombination technologies.

For example, the KSE336 locus can be disrupted in mouse ES cells using a positive-negative selection method (e.g., Mansour et al., Nature, 336:348–352, 1988). In this method, a targeting vector can be constructed which comprises a part of the gene to be targeted. A selectable marker, such as neomycin resistance genes, can be inserted into a KSE336 exon present in the targeting vector, disrupting it. When the vector recombines with the ES cell genome, it disrupts the function of the gene. The presence in the cell of the vector can be determined by expression of neomycin resistance. See, e.g., U.S. Pat. No. 6,239,326. Cells having at least one functionally disrupted gene can be used to make chimeric and germline animals, e.g., animals having somatic and/or germ cells comprising the engineered gene. Homozygous knock-out animals can be obtained from breeding heterozygous knock-out animals. See, e.g., U.S. Pat. No. 6,225,525.

A transgenic animal, or animal cell, lacking one or more functional KSE336 genes can be useful in a variety of applications, including, as an animal model for brain and pancreas diseases, for drug screening assays (e.g., for kinases other than KSE336; by making a cell deficient in KSE336, the contribution of other kinases can be specifically examined), as a source of tissues deficient in KSE336 activity, and any of the utilities mentioned in any issued U.S. patent on transgenic animals, including, U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. For instance, KSE336 deficient animal cells can be utilized to study kinase activities. Pancreas and brain cells display a variety of enzyme activities which are responsive to extracellular and intracellular signals. By knocking-out protein kinase activity, e.g., one at a time, the physiological pathways using kinase activity can be dissected out and identified.

The present invention also relates to non-human, transgenic animal whose genome comprises recombinant KSE336 nucleic acid operatively linked to an expression control sequence effective to express said coding sequence, e.g., in pancreas and brain. Such a transgenic animal can also be referred to as a "knock-in" animal since an exogenous gene has been introduced, stably, into its genome.

A recombinant KSE336 nucleic acid refers to a gene which has been introduced into a target host cell and optionally modified, such as cells derived from animals, plants, bacteria, yeast, etc. A recombinant KSE336 includes completely synthetic nucleic acid sequences, semi-synthetic nucleic acid sequences, sequences derived from natural sources, and chimeras thereof. "Operable linkage" has the meaning used through the specification, i.e., placed in a functional relationship with another nucleic acid. When a gene is operably linked to an expression control sequence, as explained above, it indicates that the gene (e.g., coding sequence) is joined to the expression control sequence (e.g., promoter) in such a way that facilitates transcription and translation of the coding sequence. As described above, the phrase "genome" indicates that the genome of the cell has been modified. In this case, the recombinant KSE336 has been stably integrated into the genome of the animal. The KSE336 nucleic acid in operable linkage with the expression control sequence can also be referred to as a construct or transgene.

Any expression control sequence can be used depending on the purpose. For instance, if selective expression is desired, then expression control sequences which limit its expression can be selected. These include, e.g., tissue or cell-specific promoters, introns, enhancers, etc. For various methods of cell and tissue-specific expression, see, e.g., U.S. Pat. Nos. 6,215,040, 6,210,736, and 6,153,427. These also include the endogenous promoter, i.e., the coding sequence can be operably linked to its own promoter. Inducible and regulatable promoters can also be utilized.

The present invention also relates to a transgenic animal which contains a functionally disrupted and a transgene stably integrated into the animals genome. Such an animal can be constructed using combinations any of the above- and below-mentioned methods. Such animals have any of the aforementioned uses, including permitting the knock-out of the normal gene and its replacement with a mutated gene. Such a transgene can be integrated at the endogenous gene locus so that the functional disruption and "knock-in" are carried out in the same step.

In addition to the methods mentioned above, transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology, cloning methods, nuclear transfer methods. See, also, e.g., U.S. Patent Nos. 4,736,866; 4,873,191; 4,873,316; 5,082,779; 5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11:1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993; Cibelli et al., Science, 280:1256–1258, 1998. For guidance on recombinase excision systems, see, e.g., U.S. Pat. Nos. 5,626,159, 5,527,695, and 5,434,066. See also, Orban, P.C., et al., "Tissue- and Site-Specific DNA Recombination in Transgenic Mice," Proc. Natl. Acad. Sci. USA, 89:6861–6865 (1992); O'Gorman, S., et al., "Recombinase-Mediated Gene Activation and Site-Specific Integration in Mammalian Cells," Science, 251:1351–1355 (1991); Sauer, B., et al., "Cre-stimulated recombination at loxP-Containing DNA sequences placed into the mammalian genome," Polynucleotides Research, 17(1):147–161 (1989); Gagneten, S. et al. (1997) Nucl. Acids Res. 25:3326–3331; Xiao and Weaver (1997) Nucl. Acids Res. 25:2985–2991; Agah, R. et al. (1997) J. Clin. Invest. 100:169–179; Barlow, C. et al. (1997) Nucl. Acids Res. 25:2543–2545; Araki, K. et al. (1997) Nucl. Acids Res. 25:868–872; Mortensen, R. N. et al. (1992) Mol. Cell. Biol. 12:2391–2395 (G418 escalation method); Lakhlani, P. P. et al. (1997) Proc. Natl. Acad. Sci. USA 94:9950–9955 ("hit and run"); Westphal and Leder (1997) Curr. Biol. 7:530–533 (transposon-generated "knock-out" and "knock-in"); Templeton, N. S. et al. (1997) Gene Ther. 4:700–709 (methods for efficient gene targeting, allowing for a high frequency of homologous recombination events, e.g., without selectable markers); PCT International Publication WO 93/22443 (functionally-disrupted).

A polynucleotide according to the present invention can be introduced into any non-human animal, including a non-human mammal, mouse (Hogan et al., *Manipulating the Mouse Embryo: A Laboratory Manual*, Cold Spring Harbor Laboratory, Cold Spring Harbor, N.Y., 1986), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988. Transgenic animals can be produced by the methods described in U.S. Pat. No. 5,994,618, and utilized for any of the utilities described therein.

The present invention relates to, e.g.,
- a non-human, transgenic mammal whose genome comprises a functional disruption of KSE336, optionally whose genome further comprises KSE336 operatively linked to an expression control sequence effective to express said gene in brain and pancreas cells, cells derived from brain and pancreas, or brain and pancreas progenitor cells. and optionally, the expression control sequence is an inducible promoter;
- a mammalian cell whose genome comprises a functional disruption of KSE336, and optionally, where the cell is a brain and pancreas, cell derived from brain and pancreas, or a brain and pancreas progenitor cell;
- a non-human, transgenic mammal whose genome comprises a recombinant KSE336 nucleic acid operatively linked to an expression control sequence effective to express said gene in brain and pancreas, cells derived from brain and pancreas, or brain and pancreas progenitor cells, optionally, where the expression control sequence is an inducible promoter, and optionally, whose genome further comprises a functional disruption of the endogenous KSE336; and
- a mammalian cell whose genome comprises a recombinant KSE336 operatively linked to an expression control sequence effective to express said gene in brain and pancreas cells, cells derived from brain and pancreas, or brain and pancreas progenitor cells.

Database

The present invention also relates to electronic forms of polynucleotides, polypeptides, etc., of the present invention, including computer-readable medium (e.g., magnetic, optical, etc., stored in any suitable format, such as flat files or hierarchical files) which comprise such sequences, or fragments thereof, e-commerce-related means, etc. Along these lines, the present invention relates to methods of retrieving gene sequences from a computer-readable medium, comprising, one or more of the following steps in any effective order, e.g., selecting a cell or gene expression profile, e.g., a profile that specifies that said gene is differentially expressed in brain and pancreas, and retrieving said differentially expressed gene sequences, where the gene sequences consist of the genes represented by SEQ ID NO 1 and 2.

A "gene expression profile" means the list of tissues, cells, etc., in which a defined gene is expressed (i.e, transcribed and/or translated). A "cell expression profile" means the genes which are expressed in the particular cell type. The profile can be a list of the tissues in which the gene is expressed, but can include additional information as well, including level of expression (e.g., a quantity as compared or normalized to a control gene), and information on temporal (e.g., at what point in the cell-cycle or developmental program) and spatial expression. By the phrase "selecting a gene or cell expression profile," it is meant that a user decides what type of gene or cell expression pattern he is interested in retrieving, e.g., he may require that the gene is differentially expressed in a tissue, or he may require that the gene is not expressed in blood, but must be expressed in brain and pancreas. Any pattern of expression preferences may be selected. The selecting can be performed by any effective method. In general, "selecting" refers to the process in which a user forms a query that is used to search a database of gene expression profiles. The step of retrieving involves searching for results in a database that correspond to the query set forth in the selecting step. Any suitable algorithm can be utilized to perform the search query, including algorithms that look for matches, or that perform optimization between query and data. The database is information that has been stored in an appropriate storage medium, having a suitable computer-readable format. Once results are retrieved, they can be displayed in any suitable format, such as HTML.

For instance, the user may be interested in identifying genes that are differentially expressed in a brain and pancreas. He may not care whether small amounts of expression occur in other tissues, as long as such genes are not expressed in peripheral blood lymphocytes. A query is formed by the user to retrieve the set of genes from the database having the desired gene or cell expression profile. Once the query is inputted into the system, a search algorithm is used to interrogate the database, and retrieve results.
Advertising, Licensing, etc., Methods The present invention also relates to methods of advertising, licensing, selling, purchasing, brokering, etc., genes, polynucleotides, specific-binding partners, antibodies, etc., of the present invention. Methods can comprises, e.g., displaying a KSE336 gene, KSE336 polypeptide, or antibody specific for KSE336 in a printed or computer-readable medium (e.g., on the Web or Internet), accepting an offer to purchase said gene, polypeptide, or antibody.
Other A polynucleotide, probe, polypeptide, antibody, specific-binding partner, etc., according to the present invention can be isolated. The term "isolated" means that the material is in a form in which it is not found in its original environment or in nature, e.g., more concentrated, more purified, separated from component, etc. An isolated polynucleotide includes, e.g., a polynucleotide having the sequenced separated from the chromosomal DNA found in a living animal, e.g., as the complete gene, a transcript, or a cDNA. This polynucleotide can be part of a vector or inserted into a chromosome (by specific gene-targeting or by random integration at a position other than its normal position) and still be isolated in that it is not in a form that is found in its natural environment. A polynucleotide, polypeptide, etc., of the present invention can also be substantially purified. By substantially purified, it is meant that polynucleotide or polypeptide is separated and is essentially free from other polynucleotides or polypeptides, i.e., the polynucleotide or polypeptide is the primary and active constituent. A polynucleotide can also be a recombinant molecule. By "recombinant," it is meant that the polynucleotide is an arrangement or form which does not occur in nature. For instance, a recombinant molecule comprising a promoter sequence would not encompass the naturally-occurring gene, but would include the promoter operably linked to a coding sequence not associated with it in nature, e.g., a reporter gene, or a truncation of the normal coding sequence.

The term "marker" is used herein to indicate a means for detecting or labeling a target. A marker can be a polynucleotide (usually referred to as a "probe"), polypeptide (e.g., an antibody conjugated to a detectable label), PNA, or any effective material.

The term "consisting essentially" indicates that a composition has ingredients that are specifically identified in the claim but other ingredients may also be present, although not specifically identified in the claim, so long as those other unlisted ingredients do not have a material effect on the basic and novel characteristics of the composition.

The topic headings set forth above are meant as guidance where certain information can be found in the application, but are not intended to be the only source in the application where information on such topic can be found.

Reference Materials

For other aspects of the polynucleotides, reference is made to standard textbooks of molecular biology. See, e.g., Hames et al., *Polynucleotide Hybridization*, IL Press, 1985; Davis et al., *Basic Methods in Molecular Biology*, Elsevir Sciences Publishing, Inc., New York, 1986; Sambrook et al., *Molecular Cloning*, CSH Press, 1989; Howe, *Gene Cloning and Manipulation*, Cambridge University Press, 1995; Ausubel et al., *Current Protocols in Molecular Biology*, John Wiley & Sons, Inc., 1994–1998.

The preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

What is claimed is:

1. An isolated polynucleotide which codes without interruption for a human KSE336 polypeptide as set forth in SEQ ID NO: 2 or SEQ ID NO: 4, or a complete complement thereto.

2. An isolated polynucleotide which has 99% or more sequence identity to a polynucleotide as set forth in SEQ ID NO: 1 or 3, or a complete complement thereto, wherein said polynucleotide encodes for a human KSE336 polypeptide having serine/threonine protein kinase activity.

3. The isolated polynucleotide of claim 1, comprising the sequence set forth in SEQ ID NO: 1.

4. The isolated polynucleotide of claim 1, comprising the sequence set forth in SEQ ID NO: 3.

5. A method for identifying an agent that modulates the expression of a polynucleotide encoding human KSE336 in brain cells, pancreas cells, brain progenitor cells, or pancreas progenitor cells, said method comprising, a) contacting a cell population comprising said cells with a test agent under conditions effective for said test agent to modulate the expression of the polynucleotide of claim 1; and, b) determining whether said test agent modulates the expression of said polynucleotide.

6. The method of claim 5, wherein said agent is an antisense polynucleotide to a target polynucleotide sequence within SEQ ID NO: 1 which is effective to inhibit translation of said human KSE336.

* * * * *

SEQUENCE LISTING

<160> NUMBER OF SEQ ID NOS: 18

<210> SEQ ID NO 1
<211> LENGTH: 2908
<212> TYPE: DNA
<213> ORGANISM: Homo sapiens
<220> FEATURE:
<221> NAME/KEY: CDS
<222> LOCATION: (106)..(2112)

<400> SEQUENCE: 1

```
ggccgggtcg gcgcggacgg cactcggcgg acgcgggcgg acgctgggcg gcccctccct      60
gcccgcgcgc ccgggcgccc ctggccggcg ccgggcccca gagcg atg aca tcg acg     117
                                                  Met Thr Ser Thr
```

-continued

|   |   |
|---|---|
| ggg aag gac ggc ggc gcg cag cac gcg cag tat gtt ggg ccc tac cgg<br>Gly Lys Asp Gly Gly Ala Gln His Ala Gln Tyr Val Gly Pro Tyr Arg<br>5                         10                    15                    20 | 165 |
| ctg gag aag acg ctg ggc aag ggg cag aca ggt ctg gtg aag ctg ggg<br>Leu Glu Lys Thr Leu Gly Lys Gly Gln Thr Gly Leu Val Lys Leu Gly<br>                     25                    30                    35 | 213 |
| gtt cac tgc gtc acc tgc cag aag gtg gcc atc aag atc gtc aac cgt<br>Val His Cys Val Thr Cys Gln Lys Val Ala Ile Lys Ile Val Asn Arg<br>            40                    45                    50 | 261 |
| gag aag ctc agc gag tcg gtg ctg atg aag gtg gag cgg gag atc gcg<br>Glu Lys Leu Ser Glu Ser Val Leu Met Lys Val Glu Arg Glu Ile Ala<br>            55                    60                    65 | 309 |
| atc ctg aag ctc att gag cac ccc cac gtc cta aag ctg cac gac gtt<br>Ile Leu Lys Leu Ile Glu His Pro His Val Leu Lys Leu His Asp Val<br>70                        75                        80 | 357 |
| tat gaa aac aaa aaa tat ttg tac ctg gtg cta gaa cac gtg tca ggt<br>Tyr Glu Asn Lys Lys Tyr Leu Tyr Leu Val Leu Glu His Val Ser Gly<br>85                        90                    95                100 | 405 |
| ggt gag ctc ttc gac tac ctg gtg aag aag ggg agg ctg acg cct aag<br>Gly Glu Leu Phe Asp Tyr Leu Val Lys Lys Gly Arg Leu Thr Pro Lys<br>                   105                  110                115 | 453 |
| gag gct cgg aag ttc ttc cgg cag atc atc tct gcg ctg gac ttc tgc<br>Glu Ala Arg Lys Phe Phe Arg Gln Ile Ile Ser Ala Leu Asp Phe Cys<br>                120                  125                130 | 501 |
| cac agc cac tcc ata tgc cac agg gat ctg aaa cct gaa aac ctc ctg<br>His Ser His Ser Ile Cys His Arg Asp Leu Lys Pro Glu Asn Leu Leu<br>              135                140                145 | 549 |
| ctg gac gag aag aac aac atc cgc atc gca gac ttt ggc atg gcg tcc<br>Leu Asp Glu Lys Asn Asn Ile Arg Ile Ala Asp Phe Gly Met Ala Ser<br>150                       155                  160 | 597 |
| ctg cag gtt ggc gac agc ctg ttg gag acc agc tgt ggg tcc ccc cac<br>Leu Gln Val Gly Asp Ser Leu Leu Glu Thr Ser Cys Gly Ser Pro His<br>165                       170                  175                180 | 645 |
| tac gcc tgc ccc gag gtg atc cgg ggg gag aag tat gac ggc cgg aag<br>Tyr Ala Cys Pro Glu Val Ile Arg Gly Glu Lys Tyr Asp Gly Arg Lys<br>                185                  190                195 | 693 |
| gcg gac gtg tgg agc tgc ggc gtc atc ctg ttc gcc ttg ctg gtg ggg<br>Ala Asp Val Trp Ser Cys Gly Val Ile Leu Phe Ala Leu Leu Val Gly<br>              200                  205                210 | 741 |
| gct ctg ccc ttc gac gat gac aac ttg cga cag ctg ctg gag aag gtg<br>Ala Leu Pro Phe Asp Asp Asp Asn Leu Arg Gln Leu Leu Glu Lys Val<br>              215                220                225 | 789 |
| aag cgg ggc gtg ttc cac atg ccg cac ttt atc ccg ccc gac tgc cag<br>Lys Arg Gly Val Phe His Met Pro His Phe Ile Pro Pro Asp Cys Gln<br>230                       235                  240 | 837 |
| agt ctg cta cgg ggc atg atc gag gtg gac gcc gca cgc cgc ctc acg<br>Ser Leu Leu Arg Gly Met Ile Glu Val Asp Ala Ala Arg Arg Leu Thr<br>245                       250                  255                260 | 885 |
| cta gag cac att cag aaa cac ata tgg tat ata ggg ggc aag aat gag<br>Leu Glu His Ile Gln Lys His Ile Trp Tyr Ile Gly Gly Lys Asn Glu<br>              265                270                275 | 933 |
| ccc gaa cca gag cag ccc att cct cgc aag gtg cag atc cgc tcg ctg<br>Pro Glu Pro Glu Gln Pro Ile Pro Arg Lys Val Gln Ile Arg Ser Leu<br>280                       285                  290 | 981 |
| ccc agc ctg gag gac atc gac ccc gac gtg ctg gac agc atg cac tca<br>Pro Ser Leu Glu Asp Ile Asp Pro Asp Val Leu Asp Ser Met His Ser<br>              295                300                305 | 1029 |
| ctg ggc tgc ttc cga gac cgc aac aag ctg ctg cag gac ctg ctg tcc | 1077 |

-continued

| | | | | | | | | | | | | | | |
|---|---|---|---|---|---|---|---|---|---|---|---|---|---|---|
|Leu|Gly|Cys|Phe|Arg|Asp|Arg|Asn|Lys|Leu|Leu|Gln|Asp|Leu|Leu|Ser|
| |310| | | | |315| | | | |320| | | |

```
gag gag gag aac cag gag aag atg att tac ttc ctc ctg gac cgg      1125
Glu Glu Glu Asn Gln Glu Lys Met Ile Tyr Phe Leu Leu Asp Arg
325                 330                 335                 340 aaa gaa agg tac ccg agc cag gag gat gag gac ctg ccc ccc cgg aac  1173
Lys Glu Arg Tyr Pro Ser Gln Glu Asp Glu Asp Leu Pro Pro Arg Asn
                345                 350                 355 gag ata gac cct ccc cgg aag cgt gtg gac tcc ccg atg ctg aac cgg  1221
Glu Ile Asp Pro Pro Arg Lys Arg Val Asp Ser Pro Met Leu Asn Arg
            360                 365                 370 cac ggc aag cgg cgg cca gaa cgc aag tcc atg gag gtg ctc agc gtg  1269
His Gly Lys Arg Arg Pro Glu Arg Lys Ser Met Glu Val Leu Ser Val
        375                 380                 385 acg gac ggc ggc tcc ccg gtg cct gcg cgg cgg gcc att gag atg gcc  1317
Thr Asp Gly Gly Ser Pro Val Pro Ala Arg Arg Ala Ile Glu Met Ala
390                 395                 400 cag cac ggc cag agg tct cgg tcc atc agc ggt gcc tcc tca ggc ctt  1365
Gln His Gly Gln Arg Ser Arg Ser Ile Ser Gly Ala Ser Ser Gly Leu
405                 410                 415                 420 tcc acc agc cca ctc agc agc ccc cgg gtg acc cct cac ccc tca cca  1413
Ser Thr Ser Pro Leu Ser Ser Pro Arg Val Thr Pro His Pro Ser Pro
                425                 430                 435 agg ggc agt ccc ctc ccc acc ccc aag ggg aca cct gtc cac acg cca  1461
Arg Gly Ser Pro Leu Pro Thr Pro Lys Gly Thr Pro Val His Thr Pro
            440                 445                 450 aag gag agc ccg gct ggc acg ccc aac ccc acg ccc ccg tcc agc ccc  1509
Lys Glu Ser Pro Ala Gly Thr Pro Asn Pro Thr Pro Pro Ser Ser Pro
        455                 460                 465 agc gtc gga ggg gtg ccc tgg agg gcg cgg ctc aac tcc atc aag aac  1557
Ser Val Gly Gly Val Pro Trp Arg Ala Arg Leu Asn Ser Ile Lys Asn
470                 475                 480 agc ttt ctg ggc tca ccc cgc ttc cac cgc cgg aaa ctg caa gtt ccg  1605
Ser Phe Leu Gly Ser Pro Arg Phe His Arg Arg Lys Leu Gln Val Pro
485                 490                 495                 500 acg ccg gag gag atg tcc aac ctg aca cca gag tcg tcc cca gag ctg  1653
Thr Pro Glu Glu Met Ser Asn Leu Thr Pro Glu Ser Ser Pro Glu Leu
                505                 510                 515 gcg aag aag tcc tgg ttt ggg aac ttc atc agc ctg gag aag gag gag  1701
Ala Lys Lys Ser Trp Phe Gly Asn Phe Ile Ser Leu Glu Lys Glu Glu
            520                 525                 530 cag atc ttc gtg gtc atc aaa gac aaa cct ctg agc tcc atc aag gct  1749
Gln Ile Phe Val Val Ile Lys Asp Lys Pro Leu Ser Ser Ile Lys Ala
        535                 540                 545 gac atc gtg cac gcc ttc ctg tcg att ccc agt ctc agc cac agc gtc  1797
Asp Ile Val His Ala Phe Leu Ser Ile Pro Ser Leu Ser His Ser Val
550                 555                 560 atc tcc caa acg agc ttc cgg gcc gag tac aag gcc acg ggg ggg cca  1845
Ile Ser Gln Thr Ser Phe Arg Ala Glu Tyr Lys Ala Thr Gly Gly Pro
565                 570                 575                 580 gcc gtg ttc cag aag ccg gtc aag ttc cag gtt gat atc acc tac acg  1893
Ala Val Phe Gln Lys Pro Val Lys Phe Gln Val Asp Ile Thr Tyr Thr
                585                 590                 595 gag ggt ggg gag gcg cag aag gag aac ggc atc tac tcc gtc acc ttc  1941
Glu Gly Gly Glu Ala Gln Lys Glu Asn Gly Ile Tyr Ser Val Thr Phe
            600                 605                 610 acc ctg ctc tca ggc ccc agc cgt cgc ttc aag agg gtg gtg gag acc  1989
Thr Leu Leu Ser Gly Pro Ser Arg Arg Phe Lys Arg Val Val Glu Thr
        615                 620                 625
```

```
atc cag gcc cag ctg ctg agc aca cac gac ccg cct gcg gcc cag cac    2037
Ile Gln Ala Gln Leu Leu Ser Thr His Asp Pro Pro Ala Ala Gln His
        630                 635                 640 ttg tca gac acc act aac tgt atg gaa atg atg acg ggg cgg ctt tcc    2085
Leu Ser Asp Thr Thr Asn Cys Met Glu Met Met Thr Gly Arg Leu Ser
645                 650                 655                 660 aaa tgt gga att atc ccg aaa agt taa catgtcacct ccacgaggcc          2132
Lys Cys Gly Ile Ile Pro Lys Ser
                665 atcctctgtg accgaaggca gctgctgcgg acccgccctc cctccgctcc tgctgttgct  2192 gccgggcagt gaggcccagc ccagcgcccc gtccaccccg cggcagctcc tcgcctcact  2252 ccgcacggcc cgtgggagga aggccaggct cgggggagcc tcctccagcc cggccgaccc  2312 ggactcccgg tcacctgacc cctcagcaag aacagcctgc ctggtggcct tctggggcca  2372 ggaccectgg tgggcaacgt agccacagga acaggccccg tccaccgcct ccacgccgca  2432 cctggaggcc tcctcgcagg cccgtgcccc gcctccctgc cgcgccgcct ccgtgtagtc  2492 ttggcctcct caggctgcct cccgtcctct cgtctcaccc gcgcctccct tgcctcatct  2552 ggggcggctg tgggctctgg cgctcctctc tggctgaggt ggaaacagag acaccctgtg  2612 gcaccagagc cttcccagca ggccaggccg ctgggctggg atcagtgtta tttatttgcc  2672 gttttaattt atggattctc cgcacctctg ttcaggaagg ggcggcggcc acatcccctg  2732 ccgtctgcgt gtctcaggca gtgggggggc tgggccagg gcgccctctg aggacagagc  2792 tggtggggcg cgggggggct ggcgagctac tgtaaacttt aaagaattcc tgcaagatat  2852 ttttataaaa aaaaaaaaaa aaaaaaaaaa aaaaaaaaaa aaaaaa                2908

<210> SEQ ID NO 2
<211> LENGTH: 668
<212> TYPE: PRT
<213> ORGANISM: Homo sapiens

<400> SEQUENCE: 2

Met Thr Ser Thr Gly Lys Asp Gly Gly Ala Gln His Ala Gln Tyr Val
1               5                   10                  15

Gly Pro Tyr Arg Leu Glu Lys Thr Leu Gly Lys Gly Gln Thr Gly Leu
            20                  25                  30

Val Lys Leu Gly Val His Cys Val Thr Cys Gln Lys Val Ala Ile Lys
        35                  40                  45

Ile Val Asn Arg Glu Lys Leu Ser Glu Ser Val Leu Met Lys Val Glu
    50                  55                  60

Arg Glu Ile Ala Ile Leu Lys Leu Ile Glu His Pro His Val Leu Lys
65                  70                  75                  80

Leu His Asp Val Tyr Glu Asn Lys Lys Tyr Leu Tyr Leu Val Leu Glu
                85                  90                  95

His Val Ser Gly Gly Glu Leu Phe Asp Tyr Leu Val Lys Lys Gly Arg
            100                 105                 110

Leu Thr Pro Lys Glu Ala Arg Lys Phe Phe Arg Gln Ile Ile Ser Ala
        115                 120                 125

Leu Asp Phe Cys His Ser His Ser Ile Cys His Arg Asp Leu Lys Pro
    130                 135                 140

Glu Asn Leu Leu Leu Asp Glu Lys Asn Asn Ile Arg Ile Ala Asp Phe
145                 150                 155                 160

Gly Met Ala Ser Leu Gln Val Gly Asp Ser Leu Leu Glu Thr Ser Cys
                165                 170                 175
```

-continued

```
Gly Ser Pro His Tyr Ala Cys Pro Glu Val Ile Arg Gly Glu Lys Tyr
            180                 185                 190

Asp Gly Arg Lys Ala Asp Val Trp Ser Cys Gly Val Ile Leu Phe Ala
            195                 200                 205

Leu Leu Val Gly Ala Leu Pro Phe Asp Asp Asp Asn Leu Arg Gln Leu
            210                 215                 220

Leu Glu Lys Val Lys Arg Gly Val Phe His Met Pro His Phe Ile Pro
225                 230                 235                 240

Pro Asp Cys Gln Ser Leu Leu Arg Gly Met Ile Glu Val Asp Ala Ala
                    245                 250                 255

Arg Arg Leu Thr Leu Glu His Ile Gln Lys His Ile Trp Tyr Ile Gly
                    260                 265                 270

Gly Lys Asn Glu Pro Glu Pro Glu Gln Pro Ile Pro Arg Lys Val Gln
            275                 280                 285

Ile Arg Ser Leu Pro Ser Leu Glu Asp Ile Asp Pro Asp Val Leu Asp
            290                 295                 300

Ser Met His Ser Leu Gly Cys Phe Arg Asp Arg Asn Lys Leu Leu Gln
305                 310                 315                 320

Asp Leu Leu Ser Glu Glu Asn Gln Glu Lys Met Ile Tyr Phe Leu
                    325                 330                 335

Leu Leu Asp Arg Lys Glu Arg Tyr Pro Ser Gln Glu Asp Glu Asp Leu
            340                 345                 350

Pro Pro Arg Asn Glu Ile Asp Pro Pro Arg Lys Arg Val Asp Ser Pro
            355                 360                 365

Met Leu Asn Arg His Gly Lys Arg Arg Pro Glu Arg Lys Ser Met Glu
            370                 375                 380

Val Leu Ser Val Thr Asp Gly Gly Ser Pro Val Pro Ala Arg Arg Ala
385                 390                 395                 400

Ile Glu Met Ala Gln His Gly Gln Arg Ser Arg Ser Ile Ser Gly Ala
                    405                 410                 415

Ser Ser Gly Leu Ser Thr Ser Pro Leu Ser Ser Pro Arg Val Thr Pro
            420                 425                 430

His Pro Ser Pro Arg Gly Ser Pro Leu Pro Thr Pro Lys Gly Thr Pro
            435                 440                 445

Val His Thr Pro Lys Glu Ser Pro Ala Gly Thr Pro Asn Pro Thr Pro
            450                 455                 460

Pro Ser Ser Pro Ser Val Gly Gly Val Pro Trp Arg Ala Arg Leu Asn
465                 470                 475                 480

Ser Ile Lys Asn Ser Phe Leu Gly Ser Pro Arg Phe His Arg Arg Lys
                    485                 490                 495

Leu Gln Val Pro Thr Pro Glu Glu Met Ser Asn Leu Thr Pro Glu Ser
            500                 505                 510

Ser Pro Glu Leu Ala Lys Lys Ser Trp Phe Gly Asn Phe Ile Ser Leu
            515                 520                 525

Glu Lys Glu Glu Gln Ile Phe Val Val Ile Lys Asp Lys Pro Leu Ser
            530                 535                 540

Ser Ile Lys Ala Asp Ile Val His Ala Phe Leu Ser Ile Pro Ser Leu
545                 550                 555                 560

Ser His Ser Val Ile Ser Gln Thr Ser Phe Arg Ala Glu Tyr Lys Ala
                    565                 570                 575

Thr Gly Gly Pro Ala Val Phe Gln Lys Pro Val Lys Phe Gln Val Asp
            580                 585                 590

Ile Thr Tyr Thr Glu Gly Gly Glu Ala Gln Lys Glu Asn Gly Ile Tyr
```

-continued

```
                 595                 600                 605
Ser Val Thr Phe Thr Leu Leu Ser Gly Pro Ser Arg Arg Phe Lys Arg
            610                 615                 620

Val Val Glu Thr Ile Gln Ala Gln Leu Leu Ser Thr His Asp Pro Pro
625                 630                 635                 640

Ala Ala Gln His Leu Ser Asp Thr Thr Asn Cys Met Glu Met Met Thr
                645                 650                 655

Gly Arg Leu Ser Lys Cys Gly Ile Ile Pro Lys Ser
            660                 665

<210> SEQ ID NO 3
<211> LENGTH: 3364
<212> TYPE: DNA
<213> ORGANISM: Homo sapiens
<220> FEATURE:
<221> NAME/KEY: CDS
<222> LOCATION: (482)..(2239)

<400> SEQUENCE: 3
ctcgacgagg cggaggcgtc gccgcgggcc aggcctcgga ctgccgcgtc ggagtggacg      60
cggggggcgg cggcgcgggc ggacgcgggc ggcgcgaagc agcggggccc gcggggggcgc    120 cccggccggg tcggcgcgga cggcactcgg cggacgcggg cggacgctgg gcggcccctc    180
cctgcccgcg cgcccgggcg cccctggccg gcgctgggcc ccagagcgat gacatcgacg    240
gggaaggacg gcgcgcgcgca gcacgcgcag tatgttgggc cctaccggct ggagaagacg    300
ctgggcaagg ggcagacagg tctggtgaag ctgggggttc actgcgtcac ctgccagaag    360
gtggccatca agatcgtcaa ccgtgagaag ctcagcgagt cggtgctgat gaaggtggag    420
cgggagatcg cgatcctgaa gctcattgag cacccccacg tcctaaagct gcacgacgtt    480 t atg aaa aca aaa aat att tgt agg tac ctg gtg cta gaa cac gtg tca    529
  Met Lys Thr Lys Asn Ile Cys Arg Tyr Leu Val Leu Glu His Val Ser
  1               5                  10                  15 ggt ggt gag ctc ttc gac tac ctg gtg aag aag ggg agg ctg acg cct      577
Gly Gly Glu Leu Phe Asp Tyr Leu Val Lys Lys Gly Arg Leu Thr Pro
                20                  25                  30 aag gag gct cgg aag ttc ttc cgg cag atc atc tct gcg ctg gac ttc      625
Lys Glu Ala Arg Lys Phe Phe Arg Gln Ile Ile Ser Ala Leu Asp Phe
            35                  40                  45 tgc cac agc cac tcc ata tgc cac agg gat ctg aaa cct gaa aac ctc      673
Cys His Ser His Ser Ile Cys His Arg Asp Leu Lys Pro Glu Asn Leu
        50                  55                  60 ctg ctg gac gag aag aac aac atc cgc atc gca gac ttt ggc atg gcg      721
Leu Leu Asp Glu Lys Asn Asn Ile Arg Ile Ala Asp Phe Gly Met Ala
65                  70                  75                  80 tcc ctg cag gtt ggc gac agc ctg ttg gag acc agc tgt ggg tcc ccc      769
Ser Leu Gln Val Gly Asp Ser Leu Leu Glu Thr Ser Cys Gly Ser Pro
                85                  90                  95 cac tac gcc tgc ccc gag gtg atc cgg ggg gag aag tat gac ggc cgg      817
His Tyr Ala Cys Pro Glu Val Ile Arg Gly Glu Lys Tyr Asp Gly Arg
            100                 105                 110 aag gcg gac gtg tgg agc tgc ggc gtc atc ctg ttc gcc ttg ctg gtg      865
Lys Ala Asp Val Trp Ser Cys Gly Val Ile Leu Phe Ala Leu Leu Val
        115                 120                 125 ggg gct ctg ccc ttc gac gat gac aac ttg cga cag ctg ctg gag aag      913
Gly Ala Leu Pro Phe Asp Asp Asp Asn Leu Arg Gln Leu Leu Glu Lys
130                 135                 140 gtg aag cgg ggc gtg ttc cac atg ccg cac ttt atc ccg ccc gac tgc      961
Val Lys Arg Gly Val Phe His Met Pro His Phe Ile Pro Pro Asp Cys
                145                 150                 155
```

```
                         145                 150                 155                 160
cag agt ctg cta cgg ggc atg atc gag gtg gac gcc gca cgc cgc ctc         1009
Gln Ser Leu Leu Arg Gly Met Ile Glu Val Asp Ala Ala Arg Arg Leu
                165                 170                 175 acg cta gag cac att cag aaa cac ata tgg tat ata ggg ggc aag aat         1057
Thr Leu Glu His Ile Gln Lys His Ile Trp Tyr Ile Gly Gly Lys Asn
            180                 185                 190 gag ccc gaa cca gag cag ccc att cct cgc aag gtg cag atc cgc tcg         1105
Glu Pro Glu Pro Glu Gln Pro Ile Pro Arg Lys Val Gln Ile Arg Ser
        195                 200                 205 ctg ccc agc ctg gag gac atc gac ccc gac gtg ctg gac agc atg cac         1153
Leu Pro Ser Leu Glu Asp Ile Asp Pro Asp Val Leu Asp Ser Met His
    210                 215                 220 tca ctg ggc tgc ttc cga gac cgc aac aag ctg ctg cag gac ctg ctg         1201
Ser Leu Gly Cys Phe Arg Asp Arg Asn Lys Leu Leu Gln Asp Leu Leu
225                 230                 235                 240 tcc gag gag gag aac cag gag aag atg att tac ttc ctc ctc ctg gac         1249
Ser Glu Glu Glu Asn Gln Glu Lys Met Ile Tyr Phe Leu Leu Leu Asp
                245                 250                 255 cgg aaa gaa agg tac ccg agc cag gag gat gag gac ctg ccc ccc cgg         1297
Arg Lys Glu Arg Tyr Pro Ser Gln Glu Asp Glu Asp Leu Pro Pro Arg
            260                 265                 270 aac gag ata gac cct ccc cgg aag cgt gtg gac tcc ccg atg ctg aac         1345
Asn Glu Ile Asp Pro Pro Arg Lys Arg Val Asp Ser Pro Met Leu Asn
        275                 280                 285 cgg cac ggc aag cgg cgg cca gaa cgc aaa tcc atg gag gtg ctc agc         1393
Arg His Gly Lys Arg Arg Pro Glu Arg Lys Ser Met Glu Val Leu Ser
    290                 295                 300 gtg acg gac ggc ggc tcc ccg gtg cct gcg cgg cgg gcc att gag atg         1441
Val Thr Asp Gly Gly Ser Pro Val Pro Ala Arg Arg Ala Ile Glu Met
305                 310                 315                 320 gcc cag cac ggc cag agg tct cgg tcc atc agc ggt gcc tcc tca ggc         1489
Ala Gln His Gly Gln Arg Ser Arg Ser Ile Ser Gly Ala Ser Ser Gly
                325                 330                 335 ctt tcc acc agc cca ctc agc agc ccc cgg gtg acc cct cac ccc tca         1537
Leu Ser Thr Ser Pro Leu Ser Ser Pro Arg Val Thr Pro His Pro Ser
            340                 345                 350 cca agg ggc agt ccc ctc ccc acc ccc aag ggg aca cct gtc cac acg         1585
Pro Arg Gly Ser Pro Leu Pro Thr Pro Lys Gly Thr Pro Val His Thr
        355                 360                 365 cca aag gag agc ccg gct ggc acg ccc aac ccc acg ccc cgt ccc agc         1633
Pro Lys Glu Ser Pro Ala Gly Thr Pro Asn Pro Thr Pro Pro Ser Ser
    370                 375                 380 ccc agc gtc gga ggg gtg ccc tgg agg gcg cgg ctc aac tcc atc aag         1681
Pro Ser Val Gly Gly Val Pro Trp Arg Ala Arg Leu Asn Ser Ile Lys
385                 390                 395                 400 aac agc ttt ctg ggc tca ccc cgc ttc cac cgc cgg aaa ctg caa gtt         1729
Asn Ser Phe Leu Gly Ser Pro Arg Phe His Arg Arg Lys Leu Gln Val
                405                 410                 415 ccg acg ccg gag gag atg tcc aac ctg aca cca gag tcg tcc cca gag         1777
Pro Thr Pro Glu Glu Met Ser Asn Leu Thr Pro Glu Ser Ser Pro Glu
            420                 425                 430 ctg gcg aag aag tcc tgg ttt ggg aac ttc atc agc ctg gag aag gag         1825
Leu Ala Lys Lys Ser Trp Phe Gly Asn Phe Ile Ser Leu Glu Lys Glu
        435                 440                 445 gag cag atc ttc gtg gtc atc aaa gac aaa cct ctg agc tcc atc aag         1873
Glu Gln Ile Phe Val Val Ile Lys Asp Lys Pro Leu Ser Ser Ile Lys
    450                 455                 460 gct gac atc gtg cac gcc ttc ctg tcg att ccc agt ctc agc cac agc         1921
```

-continued

| | | |
|---|---|---|
| Ala Asp Ile Val His Ala Phe Leu Ser Ile Pro Ser Leu Ser His Ser<br>465                          470                          475                          480 | | |
| gtc atc tcc caa acg agc ttc cgg gcc gag tac aag gcc acg ggg ggg<br>Val Ile Ser Gln Thr Ser Phe Arg Ala Glu Tyr Lys Ala Thr Gly Gly<br>                        485                            490                            495 | 1969 | |
| cca gcc gtg ttc cag aag ccg gtc aag ttc cag gtt gat atc acc tac<br>Pro Ala Val Phe Gln Lys Pro Val Lys Phe Gln Val Asp Ile Thr Tyr<br>            500                            505                          510 | 2017 | |
| acg gag ggt ggg gag gcg cag aag gag aac ggc atc tac tcc gtc acc<br>Thr Glu Gly Gly Glu Ala Gln Lys Glu Asn Gly Ile Tyr Ser Val Thr<br>        515                          520                          525 | 2065 | |
| ttc acc ctg ctc tca ggc ccc agc cgt cgc ttc aag agg gtg gtg gag<br>Phe Thr Leu Leu Ser Gly Pro Ser Arg Arg Phe Lys Arg Val Val Glu<br>530                          535                          540 | 2113 | |
| acc atc cag gcc cag ctg ctg agc aca cac gac ccg cct gcg gcc cag<br>Thr Ile Gln Ala Gln Leu Leu Ser Thr His Asp Pro Pro Ala Ala Gln<br>545                          550                          555                          560 | 2161 | |
| cac ttg tca gac acc act aac tgt atg gaa atg atg acg ggg cgg ctt<br>His Leu Ser Asp Thr Thr Asn Cys Met Glu Met Met Thr Gly Arg Leu<br>                        565                            570                          575 | 2209 | |
| tcc aaa tgt gga att atc ccg aaa agt taa catgtcacct ccacgaggcc<br>Ser Lys Cys Gly Ile Ile Pro Lys Ser<br>        580                        585 | 2259 | |
| atcctctgtg accgaaggca gctgctgcgg acccgccctc cctccgctcc tgctgttgct | 2319 | |
| gccgggcagt gaggcccagc ccagcgcccc gtccaccccg cggcagctcc tcgcctcact | 2379 | |
| ccgcacggcc cgtgggagga aggccaggct cgggggagcc tcctccagcc cggccgaccc | 2439 | |
| ggactcccgg tcacctgacc cctcagcaag aacagcctgc ctggtggcct tctggggcca | 2499 | |
| ggacccctgg tgggcaacgt agccacagga acaggccccg tccaccgcct ccacgccgca | 2559 | |
| cctggaggcc tcctcgcagg cccgtgcccc gcctccctgc cgcgccgcct ccgtgtagtc | 2619 | |
| ttggcctcct caggctgcct cccgtcctct cgtctcaccc gcgcctccct tgcctcatct | 2679 | |
| ggggcggctg tgggctctgg cgctcctctc tggctgaggt ggaaacagag acaccctgcg | 2739 | |
| gcaccagagc cttcccagca ggccaggccg ctgggctggg atcagtgtta tttatttgcc | 2799 | |
| gtttttaattt atggattctc cgcacctctg ttcaggaag gcggcggcc acatcccctg | 2859 | |
| ccgtctgcgt gtctcaggca gtgggggggc tgggccagg gcgccctctg aggacagagc | 2919 | |
| tggtggggcg cgggggggct ggcgagctac tgtaaacttt aaagaattcc tgcaagatat | 2979 | |
| ttttataaac ttttttttct tggtggtttt tggaaaaggg tgtgggggtg ggggcgccgc | 3039 | |
| tggggcaggg ccaggttttg tgttttagtc ccttgctcct gcttctttct acacacacat | 3099 | |
| ctaaagacgg tgcggctcgc tctgtcatgg gttccgtctc tctctgtgga gaagcagctc | 3159 | |
| cacctctggg ggggctcggg gcagaggggc ggtgtctcgt agcgggcggc agcgccagcg | 3219 | |
| ccctctgtc aggctggggc aatcttggtt ttgtgtccaa aggtgaaggg gtaggaggag | 3279 | |
| ggccctcagc tggcccctcc cacacacagg acggcagggg cactgtgagg cttttcttat | 3339 | |
| taaaatgaaa aaaaaaaaa aaaaa | 3364 | |

<210> SEQ ID NO 4
<211> LENGTH: 585
<212> TYPE: PRT
<213> ORGANISM: Homo sapiens

<400> SEQUENCE: 4

Met Lys Thr Lys Asn Ile Cys Arg Tyr Leu Val Leu Glu His Val Ser
1                 5                    10                   15

```
Gly Gly Glu Leu Phe Asp Tyr Leu Val Lys Lys Gly Arg Leu Thr Pro
            20                  25                  30

Lys Glu Ala Arg Lys Phe Phe Arg Gln Ile Ile Ser Ala Leu Asp Phe
        35                  40                  45

Cys His Ser His Ser Ile Cys His Arg Asp Leu Lys Pro Glu Asn Leu
        50                  55                  60

Leu Leu Asp Glu Lys Asn Asn Ile Arg Ile Ala Asp Phe Gly Met Ala
65                  70                  75                  80

Ser Leu Gln Val Gly Asp Ser Leu Leu Glu Thr Ser Cys Gly Ser Pro
                85                  90                  95

His Tyr Ala Cys Pro Glu Val Ile Arg Gly Lys Tyr Asp Gly Arg
                100                 105                 110

Lys Ala Asp Val Trp Ser Cys Gly Val Ile Leu Phe Ala Leu Leu Val
            115                 120                 125

Gly Ala Leu Pro Phe Asp Asp Asn Leu Arg Gln Leu Leu Glu Lys
        130                 135                 140

Val Lys Arg Gly Val Phe His Met Pro His Phe Ile Pro Pro Asp Cys
145                 150                 155                 160

Gln Ser Leu Leu Arg Gly Met Ile Glu Val Asp Ala Ala Arg Arg Leu
                165                 170                 175

Thr Leu Glu His Ile Gln Lys His Ile Trp Tyr Ile Gly Gly Lys Asn
                180                 185                 190

Glu Pro Glu Pro Glu Gln Pro Ile Pro Arg Lys Val Gln Ile Arg Ser
            195                 200                 205

Leu Pro Ser Leu Glu Asp Ile Asp Pro Asp Val Leu Asp Ser Met His
        210                 215                 220

Ser Leu Gly Cys Phe Arg Asp Arg Asn Lys Leu Leu Gln Asp Leu Leu
225                 230                 235                 240

Ser Glu Glu Glu Asn Gln Glu Lys Met Ile Tyr Phe Leu Leu Leu Asp
                245                 250                 255

Arg Lys Glu Arg Tyr Pro Ser Gln Glu Asp Glu Asp Leu Pro Pro Arg
            260                 265                 270

Asn Glu Ile Asp Pro Pro Arg Lys Arg Val Asp Ser Pro Met Leu Asn
            275                 280                 285

Arg His Gly Lys Arg Arg Pro Glu Arg Lys Ser Met Glu Val Leu Ser
        290                 295                 300

Val Thr Asp Gly Gly Ser Pro Val Pro Ala Arg Arg Ala Ile Glu Met
305                 310                 315                 320

Ala Gln His Gly Gln Arg Ser Arg Ser Ile Ser Gly Ala Ser Ser Gly
            325                 330                 335

Leu Ser Thr Ser Pro Leu Ser Ser Pro Arg Val Thr Pro His Pro Ser
            340                 345                 350

Pro Arg Gly Ser Pro Leu Pro Thr Pro Lys Gly Thr Pro Val His Thr
        355                 360                 365

Pro Lys Glu Ser Pro Ala Gly Thr Pro Asn Pro Thr Pro Pro Ser Ser
        370                 375                 380

Pro Ser Val Gly Gly Val Pro Trp Arg Ala Arg Leu Asn Ser Ile Lys
385                 390                 395                 400

Asn Ser Phe Leu Gly Ser Pro Arg Phe His Arg Arg Lys Leu Gln Val
                405                 410                 415

Pro Thr Pro Glu Glu Met Ser Asn Leu Thr Pro Glu Ser Ser Pro Glu
            420                 425                 430
```

```
Leu Ala Lys Lys Ser Trp Phe Gly Asn Phe Ile Ser Leu Glu Lys Glu
            435                 440                 445

Glu Gln Ile Phe Val Val Ile Lys Asp Lys Pro Leu Ser Ser Ile Lys
        450                 455                 460

Ala Asp Ile Val His Ala Phe Leu Ser Ile Pro Ser Leu Ser His Ser
465                 470                 475                 480

Val Ile Ser Gln Thr Ser Phe Arg Ala Glu Tyr Lys Ala Thr Gly Gly
                485                 490                 495

Pro Ala Val Phe Gln Lys Pro Val Lys Phe Gln Val Asp Ile Thr Tyr
            500                 505                 510

Thr Glu Gly Gly Glu Ala Gln Lys Glu Asn Gly Ile Tyr Ser Val Thr
        515                 520                 525

Phe Thr Leu Leu Ser Gly Pro Ser Arg Arg Phe Lys Arg Val Val Glu
    530                 535                 540

Thr Ile Gln Ala Gln Leu Leu Ser Thr His Asp Pro Pro Ala Ala Gln
545                 550                 555                 560

His Leu Ser Asp Thr Thr Asn Cys Met Glu Met Met Thr Gly Arg Leu
                565                 570                 575

Ser Lys Cys Gly Ile Ile Pro Lys Ser
            580                 585

<210> SEQ ID NO 5
<211> LENGTH: 213
<212> TYPE: DNA
<213> ORGANISM: Homo sapiens
<220> FEATURE:
<221> NAME/KEY: CDS
<222> LOCATION: (1)..(213)

<400> SEQUENCE: 5 atg aca tcg acg ggg aag gac ggc ggc gcg cag cac gcg cag tat gtt         48
Met Thr Ser Thr Gly Lys Asp Gly Gly Ala Gln His Ala Gln Tyr Val
1               5                   10                  15 ggg ccc tac cgg ctg gag aag acg ctg ggc aag ggg cag aca ggt ctg         96
Gly Pro Tyr Arg Leu Glu Lys Thr Leu Gly Lys Gly Gln Thr Gly Leu
            20                  25                  30 gtg aag ctg ggg gtt cac tgc gtc acc tgc cag aag gtg gcc atc aag        144
Val Lys Leu Gly Val His Cys Val Thr Cys Gln Lys Val Ala Ile Lys
        35                  40                  45 atc gtc aac cgt gag aag ctc agc gag tcg gtg ctg atg aag gtg gag        192
Ile Val Asn Arg Glu Lys Leu Ser Glu Ser Val Leu Met Lys Val Glu
    50                  55                  60 cgg gag atc gcg atc ctg aag                                            213
Arg Glu Ile Ala Ile Leu Lys
65                  70

<210> SEQ ID NO 6
<211> LENGTH: 71
<212> TYPE: PRT
<213> ORGANISM: Homo sapiens

<400> SEQUENCE: 6

Met Thr Ser Thr Gly Lys Asp Gly Gly Ala Gln His Ala Gln Tyr Val
1               5                   10                  15

Gly Pro Tyr Arg Leu Glu Lys Thr Leu Gly Lys Gly Gln Thr Gly Leu
            20                  25                  30

Val Lys Leu Gly Val His Cys Val Thr Cys Gln Lys Val Ala Ile Lys
        35                  40                  45

Ile Val Asn Arg Glu Lys Leu Ser Glu Ser Val Leu Met Lys Val Glu
```

```
        50                  55                  60
Arg Glu Ile Ala Ile Leu Lys
 65                  70
```

<210> SEQ ID NO 7
<211> LENGTH: 50
<212> TYPE: DNA
<213> ORGANISM: Homo sapiens

<400> SEQUENCE: 7
caactcctat ctaaatttca ccggcattgt ttgcagaggc agggaaaggg                    50

<210> SEQ ID NO 8
<211> LENGTH: 50
<212> TYPE: DNA
<213> ORGANISM: Homo sapiens

<400> SEQUENCE: 8
actaaaaata aaaaaaaatt agccgggcgt ggtggcgggc acctgtagtc                    50

<210> SEQ ID NO 9
<211> LENGTH: 50
<212> TYPE: DNA
<213> ORGANISM: Homo sapiens

<400> SEQUENCE: 9
gtgttctctt tatatattgc tggaattgat ttgatgtttt gttaagggat                    50

<210> SEQ ID NO 10
<211> LENGTH: 50
<212> TYPE: DNA
<213> ORGANISM: Homo sapiens

<400> SEQUENCE: 10
ctacattcag ctaaaaatgt ctgctgtccc cactcacagc agcagcagcg                    50

<210> SEQ ID NO 11
<211> LENGTH: 50
<212> TYPE: DNA
<213> ORGANISM: Homo sapiens

<400> SEQUENCE: 11
gccctgcagg gtaaaacccc cgtccagggc agccatctgc accccctcgc                    50

<210> SEQ ID NO 12
<211> LENGTH: 50
<212> TYPE: DNA
<213> ORGANISM: Homo sapiens

<400> SEQUENCE: 12
cgggatgcgc cttaatggcg ggtcgggcgg cagcgggagc tctgctgcct                    50

<210> SEQ ID NO 13
<211> LENGTH: 50
<212> TYPE: DNA
<213> ORGANISM: Homo sapiens

<400> SEQUENCE: 13
ctgggggcgc ggggcgcggg gcgcgggcct cggcggcggc ggcggcggcg                    50

<210> SEQ ID NO 14
<211> LENGTH: 50
<212> TYPE: DNA

<213> ORGANISM: Homo sapiens

<400> SEQUENCE: 14
ggcgcggggc gcgggcctcg gcggcggcgg cggcggcggc ggcggaagcc    50

<210> SEQ ID NO 15
<211> LENGTH: 15
<212> TYPE: PRT
<213> ORGANISM: Homo sapiens

<400> SEQUENCE: 15

His Met Arg Ser Ala Met Ser Gly Leu His Leu Val Lys Arg Arg
1               5                   10                  15

<210> SEQ ID NO 16
<211> LENGTH: 7
<212> TYPE: PRT
<213> ORGANISM: Homo sapiens

<400> SEQUENCE: 16

Leu Arg Arg Ala Ser Leu Gly
1               5

<210> SEQ ID NO 17
<211> LENGTH: 603
<212> TYPE: PRT
<213> ORGANISM: Homo sapiens

<400> SEQUENCE: 17

Leu Ile Glu His Pro His Val Leu Lys Leu His Asp Val Tyr Glu Asn
1               5                   10                  15

Lys Lys Tyr Leu Tyr Leu Val Leu Glu His Val Ser Gly Gly Glu Leu
                20                  25                  30

Phe Asp Tyr Leu Val Lys Lys Gly Arg Leu Thr Pro Lys Glu Ala Arg
            35                  40                  45

Lys Phe Phe Arg Gln Ile Ile Ser Ala Leu Asp Phe Cys His Ser His
        50                  55                  60

Ser Ile Cys His Arg Asp Leu Lys Pro Glu Asn Leu Leu Leu Asp Glu
65                  70                  75                  80

Lys Asn Asn Ile Arg Ile Ala Asp Phe Gly Met Ala Ser Leu Gln Val
                85                  90                  95

Gly Asp Ser Leu Leu Glu Thr Ser Cys Gly Ser Pro His Tyr Ala Cys
            100                 105                 110

Pro Glu Val Ile Arg Gly Glu Lys Tyr Asp Gly Arg Lys Ala Asp Val
        115                 120                 125

Trp Ser Cys Gly Val Ile Leu Phe Ala Leu Leu Val Gly Ala Leu Pro
130                 135                 140

Phe Asp Asp Asp Asn Leu Arg Gln Leu Leu Glu Lys Val Lys Arg Gly
145                 150                 155                 160

Val Phe His Met Pro His Phe Ile Pro Pro Asp Cys Gln Ser Leu Leu
                165                 170                 175

Arg Gly Met Ser Glu Val Asp Ala Ala Arg Arg Leu Thr Leu Glu His
            180                 185                 190

Ile Gln Lys His Ile Trp Tyr Ile Gly Gly Lys Asn Glu Pro Glu Pro
        195                 200                 205

Glu Gln Pro Ile Pro Arg Lys Val Gln Ile Arg Ser Leu Pro Ser Leu
    210                 215                 220

Glu Asp Ile Asp Pro Asp Val Leu Asp Ser Met His Ser Leu Gly Cys

-continued

```
225                 230                 235                 240

Phe Arg Asp Arg Asn Lys Leu Leu Gln Asp Leu Leu Ser Glu Glu Glu
                245                 250                 255

Asn Gln Glu Lys Met Ile Tyr Phe Leu Leu Leu Asp Arg Lys Glu Arg
            260                 265                 270

Tyr Pro Ser Gln Glu Asp Glu Asp Leu Pro Pro Arg Asn Glu Ile Asp
        275                 280                 285

Pro Pro Arg Lys Arg Val Asp Ser Pro Met Leu Asn Arg His Gly Lys
    290                 295                 300

Arg Arg Pro Glu Arg Lys Ser Met Glu Val Leu Ser Val Thr Asp Gly
305                 310                 315                 320

Gly Ser Pro Val Pro Ala Arg Arg Ala Ile Glu Met Ala Gln His Gly
                325                 330                 335

Gln Arg Ser Arg Ser Ile Ser Gly Ala Ser Ser Gly Leu Ser Thr Ser
                340                 345                 350

Pro Leu Ser Ser Pro Arg Val Thr Pro His Pro Ser Pro Arg Gly Ser
            355                 360                 365

Pro Leu Pro Thr Pro Lys Gly Thr Pro Val His Thr Pro Lys Glu Ser
        370                 375                 380

Pro Ala Gly Thr Pro Asn Pro Thr Pro Pro Ser Ser Pro Ser Val Gly
385                 390                 395                 400

Gly Val Pro Trp Arg Ala Arg Leu Asn Ser Ile Lys Asn Ser Phe Leu
                405                 410                 415

Gly Ser Pro Arg Phe His Arg Arg Lys Leu Gln Val Pro Thr Pro Glu
                420                 425                 430

Glu Met Ser Asn Leu Thr Pro Glu Ser Ser Pro Glu Leu Ala Lys Lys
            435                 440                 445

Ser Trp Phe Gly Asn Phe Ile Ser Leu Glu Lys Glu Glu Gln Ile Phe
        450                 455                 460

Val Val Ile Lys Asp Lys Pro Leu Ser Ser Ile Lys Ala Asp Ile Val
465                 470                 475                 480

His Ala Phe Leu Ser Ile Pro Ser Leu Ser His Ser Val Ile Ser Gln
                485                 490                 495

Thr Ser Phe Arg Ala Glu Tyr Lys Ala Thr Gly Gly Pro Ala Val Phe
            500                 505                 510

Gln Lys Pro Val Lys Phe Gln Val Asp Ile Thr Tyr Thr Glu Gly Gly
        515                 520                 525

Glu Ala Gln Lys Glu Asn Gly Ile Tyr Ser Val Thr Phe Thr Leu Leu
    530                 535                 540

Ser Gly Pro Ser Arg Arg Phe Lys Arg Val Val Glu Thr Ile Gln Ala
545                 550                 555                 560

Gln Leu Leu Ser Thr His Asp Pro Pro Ala Ala Gln His Leu Ser Glu
                565                 570                 575

Pro Pro Pro Pro Ala Pro Gly Leu Ser Trp Gly Ala Gly Leu Lys Gly
            580                 585                 590

Gln Lys Val Ala Thr Ser Tyr Glu Ser Ser Leu
        595                 600
```

<210> SEQ ID NO 18
<211> LENGTH: 149
<212> TYPE: PRT
<213> ORGANISM: Homo sapiens

<400> SEQUENCE: 18

-continued

```
Met Ser Asn Leu Thr Pro Glu Ser Ser Pro Glu Leu Ala Lys Lys Ser
1               5                   10                  15

Trp Phe Gly Asn Phe Ile Ser Leu Glu Lys Glu Glu Gln Ile Phe Val
            20                  25                  30

Val Ile Lys Asp Lys Pro Leu Ser Ser Ile Lys Ala Asp Ile Val His
            35                  40              45

Ala Phe Leu Ser Ile Pro Ser Leu Ser His Ser Val Ile Ser Gln Thr
        50                  55              60

Ser Phe Arg Ala Glu Tyr Lys Ala Thr Gly Gly Pro Ala Val Phe Gln
65              70                  75                      80

Lys Pro Val Lys Phe Gln Val Asp Ile Thr Tyr Thr Glu Gly Gly Glu
                85                  90              95

Ala Gln Lys Glu Asn Gly Ile Tyr Ser Val Thr Phe Thr Leu Leu Ser
            100                 105                 110

Gly Pro Ser Arg Arg Phe Lys Arg Val Val Glu Thr Ile Gln Ala Gln
            115                 120                 125

Leu Leu Ser Thr His Asp Pro Leu Arg Pro Ser Thr Cys Gln Thr Pro
    130                 135                 140

Leu Thr Val Trp Lys
145
```